(12) United States Patent
Burwinkel et al.

(10) Patent No.: US 12,661,018 B2
(45) Date of Patent: Jun. 23, 2026

(54) MONITORING SYSTEM AND METHOD OF USING SAME

(71) Applicant: Starkey Laboratories, Inc., Eden Prairie, MN (US)

(72) Inventors: Justin R. Burwinkel, Eden Prairie, MN (US); Buye Xu, Sammamish, WA (US); Jason A. Galster, Studio City, CA (US); Lauren Petley, Cincinnati, OH (US); Peter J. Tetrick, Chaska, MN (US); Sourav K. Bhunia, Shoreview, MN (US); Peggi S. Cross, Tucson, AZ (US); Martin McKinney, Minneapolis, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 348 days.

(21) Appl. No.: 17/600,370

(22) PCT Filed: Apr. 2, 2020

(86) PCT No.: PCT/US2020/026435
§ 371 (c)(1),
(2) Date: Sep. 30, 2021

(87) PCT Pub. No.: WO2020/206155
PCT Pub. Date: Oct. 8, 2020

(65) Prior Publication Data
US 2022/0248970 A1 Aug. 11, 2022

Related U.S. Application Data

(60) Provisional application No. 62/828,766, filed on Apr. 3, 2019.

(51) Int. Cl.
*A61B 5/0205* (2006.01)
*A61B 3/113* (2006.01)
(Continued)

(52) U.S. Cl.
CPC .......... *A61B 5/02055* (2013.01); *A61B 3/113* (2013.01); *A61B 5/0002* (2013.01);
(Continued)

(58) Field of Classification Search
CPC ..... A61B 5/14535; A61B 5/16; A61B 5/4023; A61B 5/4076; A61B 5/4561;
(Continued)

(56) References Cited

U.S. PATENT DOCUMENTS

| | | | |
|---|---|---|---|
| 5,913,310 A | 6/1999 | Brown | |
| 6,186,145 B1 | 2/2001 | Brown | |
| (Continued) | | | |

FOREIGN PATENT DOCUMENTS

| | | |
|---|---|---|
| EP | 0799597 | 10/1997 |
| EP | 1229508 | 8/2002 |
| (Continued) | | |

OTHER PUBLICATIONS

"Communication Pursuant to Article 94(3) EPC," for European Patent Application No. 17838110.9 mailed Feb. 1, 2022 (8 pages).
(Continued)

*Primary Examiner* — Amanda L Steinberg
(74) *Attorney, Agent, or Firm* — Pauly, DeVries Smith & Deffner LLC

(57) ABSTRACT

Various embodiments of a monitoring system are disclosed. The monitoring system includes first and second sensors each adapted to detect a characteristic of a subject of the system and generate data representative of the characteristic of the subject, and a controller operatively connected to the first and second sensors. The controller is adapted to receive data representative of first and second characteristics of the subject from the first and second sensors, and determine statistics for first and second condition substates of the subject over a monitoring time period based upon the data
(Continued)

received from the first and second sensors. The controller is further adapted to compare the statistics of the first and second condition substates, confirm the first condition substate if it is substantially similar to the second condition substate, and determine the statistics of an overall condition state of the subject based upon the confirmed first condition substate.

19 Claims, 3 Drawing Sheets

(51) Int. Cl.

| | |
|---|---|
| A61B 5/00 | (2006.01) |
| A61B 5/021 | (2006.01) |
| A61B 5/024 | (2006.01) |
| A61B 5/11 | (2006.01) |
| A61B 5/145 | (2006.01) |
| A61B 5/1455 | (2006.01) |
| A61B 5/16 | (2006.01) |
| G08B 21/04 | (2006.01) |

(52) U.S. Cl.
CPC .............. *A61B 5/021* (2013.01); *A61B 5/024* (2013.01); *A61B 5/1112* (2013.01); *A61B 5/1114* (2013.01); *A61B 5/112* (2013.01); *A61B 5/14532* (2013.01); *A61B 5/14535* (2013.01); *A61B 5/14551* (2013.01); *A61B 5/16* (2013.01); *A61B 5/4023* (2013.01); *A61B 5/4076* (2013.01); *A61B 5/4561* (2013.01); *A61B 5/4875* (2013.01); *A61B 5/7275* (2013.01); *A61B 5/7282* (2013.01); *G08B 21/043* (2013.01); *G08B 21/0446* (2013.01); *A61B 2562/0219* (2013.01)

(58) Field of Classification Search
CPC .......... A61B 5/4875; A61B 2562/0219; A61B 3/113; G08B 21/043; G08B 21/0446
See application file for complete search history.

(56) References Cited

U.S. PATENT DOCUMENTS

| | | | |
|---|---|---|---|
| 6,326,918 B1 | 12/2001 | Stewart | |
| 6,475,161 B2 | 11/2002 | Teicher et al. | |
| 6,568,396 B1 | 5/2003 | Anthony | |
| 6,609,523 B1 | 8/2003 | Anthony | |
| 6,647,257 B2 | 11/2003 | Owensby | |
| D487,409 S | 3/2004 | Philipson | |
| 6,758,218 B2 | 7/2004 | Anthony | |
| 6,816,878 B1 | 11/2004 | Zimmers et al. | |
| 6,836,667 B1 | 12/2004 | Smith | |
| 7,007,327 B2 | 3/2006 | Ogawa et al. | |
| 7,139,820 B1 | 11/2006 | O'Toole et al. | |
| 7,282,031 B2 | 10/2007 | Hendrich | |
| 7,294,107 B2 | 11/2007 | Simon et al. | |
| 7,411,493 B2 | 8/2008 | Smith | |
| 7,450,954 B2 | 11/2008 | Randall | |
| 7,490,611 B2 | 2/2009 | Bromwich | |
| 7,602,930 B2 | 10/2009 | Kasztelan | |
| 7,612,681 B2 | 11/2009 | Azzaro et al. | |
| 7,682,308 B2 | 3/2010 | Hendrich | |
| 7,742,774 B2 | 6/2010 | Oh et al. | |
| 7,837,472 B1 | 11/2010 | Elsmore et al. | |
| 7,892,180 B2 | 2/2011 | Epley | |
| 7,899,621 B2 | 3/2011 | Breed et al. | |
| 8,092,398 B2 | 1/2012 | Weinberg et al. | |
| 8,150,044 B2 | 4/2012 | Goldstein et al. | |
| 8,162,846 B2 | 4/2012 | Epley | |
| 8,169,938 B2 | 5/2012 | Duchscher et al. | |
| 8,308,665 B2 | 11/2012 | Harry et al. | |
| 8,442,245 B2 | 5/2013 | Wurzbacher et al. | |
| 8,452,273 B1 | 5/2013 | Khomenko et al. | |
| 8,494,507 B1 | 7/2013 | Tedesco et al. | |
| 8,559,914 B2 | 10/2013 | Jones | |
| 8,585,589 B1 | 11/2013 | Cinberg | |
| 8,652,040 B2 | 2/2014 | LeBoeuf et al. | |
| 8,737,951 B2 | 5/2014 | Jones et al. | |
| 8,784,309 B2 | 7/2014 | Kahn et al. | |
| 9,049,558 B2 | 6/2015 | Jones et al. | |
| 9,149,222 B1 | 10/2015 | Zets et al. | |
| 9,167,356 B2 | 10/2015 | Higgins et al. | |
| 9,179,862 B2 | 11/2015 | Stergiou et al. | |
| 9,210,518 B2 | 12/2015 | Zhang | |
| 9,216,132 B2 | 12/2015 | Aoki et al. | |
| 9,219,964 B2 | 12/2015 | Merks | |
| D747,554 S | 1/2016 | Daniel | |
| 9,226,706 B2 | 1/2016 | Uehara et al. | |
| 9,313,585 B2 | 4/2016 | Lunner | |
| 9,392,966 B2 | 7/2016 | Ten Kate | |
| 9,414,784 B1 | 8/2016 | Berme et al. | |
| 9,426,582 B2 | 8/2016 | Pontoppidan | |
| 9,452,101 B2 | 9/2016 | Tomlinson et al. | |
| 9,605,390 B2 | 3/2017 | Penland | |
| 9,607,498 B2 | 3/2017 | Osorio | |
| 9,769,577 B2 | 9/2017 | Shennib | |
| 9,848,273 B1 | 12/2017 | Helwani et al. | |
| 9,877,668 B1 | 1/2018 | Sarkar et al. | |
| 9,918,663 B2 | 3/2018 | Singhatat | |
| 9,936,916 B2 | 4/2018 | Sahin | |
| 9,999,377 B2 | 6/2018 | Osorio | |
| 10,015,579 B2 | 7/2018 | Boesen | |
| 10,140,833 B1 | 11/2018 | Jacobson et al. | |
| 10,149,798 B2 | 12/2018 | Roth | |
| 10,178,970 B2 | 1/2019 | Oddsson et al. | |
| 10,242,590 B2 | 3/2019 | Yu | |
| 10,258,257 B2 | 4/2019 | Greene | |
| 10,262,517 B2 | 4/2019 | Bobda | |
| 10,271,790 B2 | 4/2019 | Lee | |
| 10,319,209 B2 | 6/2019 | Carlton-Foss | |
| 10,587,964 B2 | 3/2020 | Shennib | |
| 10,624,559 B2 | 4/2020 | Bhunia et al. | |
| 10,799,698 B2 | 10/2020 | Howard | |
| 10,925,518 B1 | 2/2021 | Najafi et al. | |
| 10,974,049 B1 * | 4/2021 | Heldman ........... A61N 1/36132 |
| 11,277,697 B2 | 3/2022 | Burwinkel et al. | |
| 11,559,251 B2 | 1/2023 | Burwinkel et al. | |
| 11,638,563 B2 | 5/2023 | Burwinkel et al. | |
| 12,149,893 B2 | 11/2024 | Burwinkel et al. | |
| 12,254,755 B2 | 3/2025 | Burwinkel et al. | |
| 12,313,762 B2 | 5/2025 | Bhowmik et al. | |
| 12,484,860 B2 | 12/2025 | Burwinkel et al. | |
| 2002/0188217 A1 | 12/2002 | Farwell | |
| 2004/0234933 A1 | 11/2004 | Dawson et al. | |
| 2005/0046576 A1 | 3/2005 | Julian et al. | |
| 2005/0240378 A1 | 10/2005 | Smith et al. | |
| 2005/0273017 A1 | 12/2005 | Gordon | |
| 2006/0036141 A1 | 2/2006 | Kamath et al. | |
| 2006/0250260 A1 | 11/2006 | Albert et al. | |
| 2006/0251334 A1 | 11/2006 | Oba et al. | |
| 2006/0282021 A1 | 12/2006 | DeVaul et al. | |
| 2007/0177103 A1 | 8/2007 | Migliaccio et al. | |
| 2007/0197881 A1 | 8/2007 | Wolf et al. | |
| 2007/0200927 A1 | 8/2007 | Krenik | |
| 2007/0276270 A1 | 11/2007 | Tran | |
| 2008/0021731 A1 | 1/2008 | Rodgers | |
| 2008/0082022 A1 | 4/2008 | Brohan et al. | |
| 2008/0111677 A1 | 5/2008 | Kolz et al. | |
| 2008/0129518 A1 | 6/2008 | Carlton-Foss | |
| 2008/0146890 A1 | 6/2008 | LeBoeuf et al. | |
| 2008/0186189 A1 | 8/2008 | Azzaro et al. | |
| 2008/0243005 A1 | 10/2008 | Jung et al. | |
| 2008/0275349 A1 | 11/2008 | Halperin et al. | |
| 2009/0058660 A1 | 3/2009 | Torch | |
| 2009/0232357 A1 | 9/2009 | Angell et al. | |
| 2009/0240170 A1 | 9/2009 | Rowley et al. | |
| 2009/0240172 A1 | 9/2009 | Fernandez et al. | |
| 2009/0299622 A1 | 12/2009 | Denaro | |
| 2009/0322513 A1 | 12/2009 | Hwang et al. | |
| 2010/0010832 A1 | 1/2010 | Boute et al. | |
| 2010/0049095 A1 | 2/2010 | Bunn et al. | |

(56) References Cited

U.S. PATENT DOCUMENTS

| | | | |
|---|---|---|---|
| 2010/0075806 A1 | 3/2010 | Montgomery | |
| 2010/0141439 A1 | 6/2010 | Lunner | |
| 2010/0179389 A1 | 7/2010 | Moroney et al. | |
| 2010/0331721 A1* | 12/2010 | Epley | A61B 5/4839 |
| | | | 600/558 |
| 2011/0106627 A1 | 5/2011 | Leboeuf et al. | |
| 2011/0313315 A1 | 12/2011 | Attias et al. | |
| 2012/0075464 A1 | 3/2012 | Derenne et al. | |
| 2012/0092156 A1 | 4/2012 | Tran | |
| 2012/0101411 A1 | 4/2012 | Hausdorff et al. | |
| 2012/0119904 A1 | 5/2012 | Boone et al. | |
| 2012/0219180 A1 | 8/2012 | Mehra | |
| 2012/0232414 A1 | 9/2012 | Mollicone et al. | |
| 2012/0304767 A1 | 12/2012 | Howard et al. | |
| 2013/0065569 A1 | 3/2013 | Leipzig et al. | |
| 2013/0091016 A1 | 4/2013 | Shutter | |
| 2013/0135097 A1 | 5/2013 | Doezema | |
| 2013/0343584 A1 | 12/2013 | Bennett et al. | |
| 2013/0343585 A1 | 12/2013 | Bennett et al. | |
| 2014/0002586 A1 | 1/2014 | Nourbakhsh | |
| 2014/0023216 A1 | 1/2014 | Solum et al. | |
| 2014/0024972 A1 | 1/2014 | Greene | |
| 2014/0031703 A1 | 1/2014 | Rayner et al. | |
| 2014/0046209 A1* | 2/2014 | Klap | A61B 5/1115 |
| | | | 600/534 |
| 2014/0064528 A1 | 3/2014 | Flood et al. | |
| 2014/0074180 A1 | 3/2014 | Heldman et al. | |
| 2014/0145848 A1 | 5/2014 | Amir | |
| 2014/0148733 A1 | 5/2014 | Stone et al. | |
| 2014/0257051 A1 | 9/2014 | Cam et al. | |
| 2014/0266988 A1 | 9/2014 | Fisher et al. | |
| 2014/0276238 A1 | 9/2014 | Osorio | |
| 2014/0341408 A1 | 11/2014 | Varghese et al. | |
| 2015/0018724 A1 | 1/2015 | Hsu et al. | |
| 2015/0040685 A1 | 2/2015 | Nicholson et al. | |
| 2015/0106026 A1 | 4/2015 | Goldstein | |
| 2015/0112151 A1 | 4/2015 | Muhsin et al. | |
| 2015/0112162 A1 | 4/2015 | Wilmink | |
| 2015/0164383 A1 | 6/2015 | Varsavsky et al. | |
| 2015/0170296 A1 | 6/2015 | Kautz et al. | |
| 2015/0196231 A1 | 7/2015 | Ziaie et al. | |
| 2015/0209212 A1 | 7/2015 | Duguid | |
| 2015/0226621 A1 | 8/2015 | Zhu et al. | |
| 2015/0257662 A1 | 9/2015 | Lee et al. | |
| 2015/0269824 A1 | 9/2015 | Zhang | |
| 2015/0319546 A1 | 11/2015 | Sprague | |
| 2015/0351690 A1 | 12/2015 | Toth et al. | |
| 2016/0015289 A1 | 1/2016 | Simon et al. | |
| 2016/0029938 A1 | 2/2016 | Shudo | |
| 2016/0033280 A1 | 2/2016 | Moore et al. | |
| 2016/0038738 A1 | 2/2016 | Naylor | |
| 2016/0057550 A1 | 2/2016 | Shennib | |
| 2016/0070122 A1 | 3/2016 | Sales et al. | |
| 2016/0100776 A1 | 4/2016 | Najafi et al. | |
| 2016/0106346 A1 | 4/2016 | Benzel et al. | |
| 2016/0155312 A1 | 6/2016 | Osorio | |
| 2016/0166190 A1 | 6/2016 | Publicover et al. | |
| 2016/0262608 A1 | 9/2016 | Krueger | |
| 2016/0262694 A1 | 9/2016 | Calcano et al. | |
| 2016/0263437 A1 | 9/2016 | Kow et al. | |
| 2016/0275805 A1 | 9/2016 | Reichow | |
| 2016/0295978 A1 | 10/2016 | Hyde et al. | |
| 2016/0373869 A1 | 12/2016 | Gran et al. | |
| 2017/0000387 A1 | 1/2017 | Forth et al. | |
| 2017/0006931 A1* | 1/2017 | Guez | A61B 5/369 |
| 2017/0007147 A1 | 1/2017 | Hasegawa | |
| 2017/0055917 A1 | 3/2017 | Stone et al. | |
| 2017/0071532 A1 | 3/2017 | Greco | |
| 2017/0112671 A1 | 4/2017 | Goldstein | |
| 2017/0113057 A1 | 4/2017 | Goodall et al. | |
| 2017/0116846 A1 | 4/2017 | Wengrovitz et al. | |
| 2017/0127196 A1 | 5/2017 | Blum et al. | |
| 2017/0140637 A1 | 5/2017 | Thurlow et al. | |
| 2017/0156965 A1 | 6/2017 | Geisinger et al. | |
| 2017/0169716 A1 | 6/2017 | Super et al. | |
| 2017/0172465 A1 | 6/2017 | Osorio | |
| 2017/0188895 A1 | 7/2017 | Nathan | |
| 2017/0197115 A1 | 7/2017 | Cook et al. | |
| 2017/0229041 A1 | 8/2017 | Reichow et al. | |
| 2017/0273616 A1 | 9/2017 | Yang et al. | |
| 2017/0274219 A1 | 9/2017 | Ernst et al. | |
| 2017/0291065 A1 | 10/2017 | Klopman | |
| 2017/0352240 A1 | 12/2017 | Carlton-Foss | |
| 2017/0358195 A1 | 12/2017 | Bobda | |
| 2017/0358241 A1 | 12/2017 | Wexler et al. | |
| 2017/0360364 A1 | 12/2017 | Heasman et al. | |
| 2018/0000385 A1* | 1/2018 | Heaton | G08B 25/016 |
| 2018/0046833 A1* | 2/2018 | Havas | G06K 7/10386 |
| 2018/0092572 A1 | 4/2018 | Sanchez et al. | |
| 2018/0093121 A1 | 4/2018 | Matsuura et al. | |
| 2018/0110466 A1 | 4/2018 | Ralston | |
| 2018/0132757 A1 | 5/2018 | Kong et al. | |
| 2018/0133507 A1 | 5/2018 | Malchano et al. | |
| 2018/0177436 A1 | 6/2018 | Chang et al. | |
| 2018/0202813 A1 | 7/2018 | Belt et al. | |
| 2018/0228404 A1 | 8/2018 | Bhunia et al. | |
| 2018/0228405 A1 | 8/2018 | Burwinkel et al. | |
| 2018/0233018 A1 | 8/2018 | Burwinkel et al. | |
| 2018/0233028 A1 | 8/2018 | Rhoads et al. | |
| 2018/0234781 A1 | 8/2018 | Stewart et al. | |
| 2018/0242859 A1 | 8/2018 | LeBoeuf et al. | |
| 2018/0250494 A1 | 9/2018 | Hanbury | |
| 2018/0279915 A1 | 10/2018 | Huang et al. | |
| 2018/0279919 A1 | 10/2018 | Bansbach et al. | |
| 2018/0289287 A1 | 10/2018 | Sio et al. | |
| 2018/0317837 A1 | 11/2018 | Burwinkel et al. | |
| 2018/0333558 A1* | 11/2018 | Levendowski | A61B 5/4076 |
| 2018/0336773 A1* | 11/2018 | Hanson | G06T 7/194 |
| 2018/0341582 A1 | 11/2018 | Moon et al. | |
| 2018/0343527 A1 | 11/2018 | Edwards | |
| 2018/0373841 A1 | 12/2018 | Harpale | |
| 2019/0008435 A1 | 1/2019 | Cakmak | |
| 2019/0015046 A1 | 1/2019 | Whitehouse et al. | |
| 2019/0043610 A1* | 2/2019 | Vaughan | A61B 5/4088 |
| 2019/0066477 A1* | 2/2019 | Peyrard | G08B 21/043 |
| 2019/0103007 A1* | 4/2019 | Tan | A61B 5/1117 |
| 2019/0117121 A1 | 4/2019 | Kutina et al. | |
| 2019/0246890 A1 | 8/2019 | Kerasidis et al. | |
| 2020/0086133 A1 | 3/2020 | Wang et al. | |
| 2020/0138364 A1 | 5/2020 | Fabry et al. | |
| 2020/0143703 A1 | 5/2020 | Fabry et al. | |
| 2020/0159960 A1* | 5/2020 | Jakobsson | G06F 21/6245 |
| 2020/0187829 A1* | 6/2020 | Mohamed Elmahdy | |
| | | | A61B 5/1117 |
| 2020/0205746 A1 | 7/2020 | Burwinkel et al. | |
| 2020/0219373 A1 | 7/2020 | Stut et al. | |
| 2020/0236479 A1 | 7/2020 | Burwinkel et al. | |
| 2020/0245869 A1 | 8/2020 | Sivan et al. | |
| 2020/0268260 A1 | 8/2020 | Tran | |
| 2020/0273566 A1 | 8/2020 | Bhowmik et al. | |
| 2022/0031195 A1 | 2/2022 | Hu et al. | |
| 2022/0034495 A1 | 2/2022 | Chen et al. | |
| 2022/0248153 A1 | 8/2022 | Burwinkel et al. | |
| 2022/0361787 A1 | 11/2022 | Burwinkel et al. | |
| 2023/0397891 A1 | 12/2023 | Talebanpour et al. | |
| 2023/0404490 A1 | 12/2023 | Burwinkel et al. | |
| 2024/0000315 A1 | 1/2024 | Shahar et al. | |
| 2026/0130632 A1 | 5/2026 | Burwinkel et al. | |

FOREIGN PATENT DOCUMENTS

| | | |
|---|---|---|
| EP | 1628504 | 2/2006 |
| EP | 2104366 | 9/2009 |
| EP | 2700907 | 2/2014 |
| EP | 2725818 | 4/2014 |
| EP | 3075306 | 10/2016 |
| EP | 3131027 | 2/2017 |
| EP | 1983896 | 6/2017 |
| EP | 3246888 | 11/2017 |
| EP | 3328277 | 6/2018 |
| EP | 3346402 | 7/2018 |
| EP | 3402218 | 11/2018 |
| EP | 3591990 | 1/2020 |
| EP | 3669765 | 6/2020 |

(56)                References Cited

FOREIGN PATENT DOCUMENTS

| WO | 2008143908 | 11/2008 |
| WO | 2009053184 | 4/2009 |
| WO | 2010046504 | 4/2010 |
| WO | 2010049543 | 5/2010 |
| WO | 2010108287 | 9/2010 |
| WO | 2012083102 | 6/2012 |
| WO | 2015164456 | 10/2015 |
| WO | 2016088027 | 6/2016 |
| WO | 2016097746 | 6/2016 |
| WO | 2016110804 | 7/2016 |
| WO | 2016123129 | 8/2016 |
| WO | 2017023864 | 2/2017 |
| WO | 2018093765 | 5/2018 |
| WO | 2018127851 | 7/2018 |
| WO | 2018147942 | 8/2018 |
| WO | 2018147943 | 8/2018 |
| WO | 2018148713 | 8/2018 |
| WO | 2018223505 | 12/2018 |
| WO | 2019073473 | 4/2019 |
| WO | 2019086997 | 5/2019 |
| WO | 2020097353 | 5/2020 |
| WO | 2020097355 | 5/2020 |
| WO | 2020124022 | 6/2020 |
| WO | 2020139850 | 7/2020 |
| WO | 2020206155 | 10/2020 |
| WO | 2021016094 | 1/2021 |
| WO | 2022094089 | 5/2022 |
| WO | 2022103954 | 5/2022 |

OTHER PUBLICATIONS

"Communication Pursuant to Article 94(3) EPC," for European Patent Application No. 19839777.0 mailed Aug. 18, 2023 (5 pages).

"Communication Pursuant to Article 94(3) EPC," for European Patent Application No. 20754071.1 mailed Aug. 11, 2023 (5 pages).

"Final Office Action," for U.S. Appl. No. 15/858,680 mailed Aug. 12, 2022 (19 pages).

"Final Office Action," for U.S. Appl. No. 15/858,680 mailed Jun. 21, 2023 (25 pages).

"Final Office Action," for U.S. Appl. No. 15/895,311 mailed Jul. 18, 2022 (15 pages).

"Final Office Action," for U.S. Appl. No. 15/895,311 mailed May 8, 2023 (25 pages).

"Final Office Action," for U.S. Appl. No. 16/725,766 mailed Mar. 7, 2022 (19 pages).

"International Preliminary Report on Patentability," for PCT Application No. PCT/US2020/042571 mailed Feb. 3, 2022 (14 pages).

"International Preliminary Report on Patentability," for PCT Application No. PCT/US2021/057064 mailed May 11, 2023 (11 pages).

"International Preliminary Report on Patentability," for PCT Application No. PCT/US2021/058971 mailed May 25, 2023 (12 pages).

"International Search Report and Written Opinion," for PCT Application No. PCT/US2020/042571 mailed Nov. 25, 2020 (20 pages).

"International Search Report and Written Opinion," for PCT Application No. PCT/US2021/057064 mailed Feb. 10, 2022 (15 pages).

"International Search Report and Written Opinion," for PCT Application No. PCT/US2021/058971 mailed Mar. 3, 2022 (17 pages).

"Invitation to Pay Additional Fees," for PCT Application No. PCT/US2020/042571 mailed Sep. 16, 2020 (15 pages).

"Non-Final Office Action," for U.S. Appl. No. 15/858,680 mailed Apr. 8, 2022 (22 pages).

"Non-Final Office Action," for U.S. Appl. No. 15/858,680 mailed Jan. 25, 2023 (23 pages).

"Non-Final Office Action," for U.S. Appl. No. 15/895,311 mailed Dec. 28, 2022 (21 pages).

"Non-Final Office Action," for U.S. Appl. No. 15/895,311 mailed Feb. 9, 2022 (17 pages).

"Non-Final Office Action," for U.S. Appl. No. 16/725,766 mailed Jun. 24, 2022 (16 pages).

"Notice of Allowance," for U.S. Appl. No. 16/725,766 mailed Dec. 23, 2022 (12 pages).

"Response to Final Office Action," for U.S. Appl. No. 15/858,680 filed Nov. 11, 2022 (10 pages).

"Response to Final Office Action," for U.S. Appl. No. 15/895,311 filed Jul. 28, 2023 (16 pages).

"Response to Final Office Action," for U.S. Appl. No. 15/895,311 filed Oct. 18, 2022 (10 pages).

"Response to Final Office Action," for U.S. Appl. No. 16/725,766 filed Jun. 7, 2022 (8 pages).

"Response to Non-Final Office Action," for U.S. Appl. No. 15/858,680 filed Apr. 20, 2023 (12 pages).

"Response to Non-Final Office Action," for U.S. Appl. No. 15/858,680 filed Jul. 8, 2022 (10 pages).

"Response to Non-Final Office Action," for U.S. Appl. No. 15/895,311 filed Jun. 9, 2022 (9 pages).

"Response to Non-Final Office Action," for U.S. Appl. No. 15/895,311 filed Mar. 20, 2023 (15 pages).

"Response to Non-Final Office Action," for U.S. Appl. No. 16/725,766 filed Sep. 23, 2022 (9 pages).

"Understanding Heart Disease," WebMD Heart Disease Guide Written by WebMD Editorial Contributors and medically reviewed by James Beckerman, published at https://www.webmd.com/heart-disease/understanding-heart-disease-symptoms at least as early as Mar. 2007 (10 pages).

Raj, Rahul, et al. "Factors correlating with delayed trauma center admission following traumatic brain injury," Scandinavian Journal of Trauma, Resuscitation and Emergency Medicine 2013, 21:67 (9 pages).

Tinetti, Mary E., et al. "Antihypertensive Medications and Serious Fall Injuries in a Nationally Representative Sample of Older Adults," JAMA Intern. Med. Apr. 2014; 174(4): 588-595 (16 pages).

Wen, Jiaqu, et al. "We Help You Watch Your Steps: Unobtrusive Alertness System for Pedestrian Mobile Phone Users," 2015, IEEE International Conference on Pervasive Computing and Communications (PerCom), pp. 105-113 (9 pages).

"European Search Report," for European Patent Application No. 19212657.1 mailed Feb. 14, 2020 (10 pages).

File History for U.S. Appl. No. 16/714,339 downloaded Dec. 1, 2021 (277 pages).

File History for U.S. Appl. No. 15/589,298 downloaded Dec. 1, 2021 (381 pages).

File History for U.S. Appl. No. 15/895,311 downloaded Dec. 1, 2021 (287 pages).

File History for U.S. Appl. No. 15/858,630 downloaded Dec. 1, 2021 (754 pages).

File History for U.S. Appl. No. 15/858,680 downloaded Dec. 1, 2021 (795 pages).

File History for U.S. Appl. No. 16/725,766 downloaded Dec. 1, 2021 (136 pages).

"International Preliminary Report on Patentability," for PCT Application No. PCT/US2017/069026 mailed Aug. 22, 2019 (9 pages).

"International Preliminary Report on Patentability," for PCT Application No. PCT/US2017/0690365 mailed Aug. 22, 2019 (9 pages).

"International Preliminary Report on Patentability," for PCT Application No. PCT/US2018/017944 mailed Aug. 22, 2019 (7 pages).

"International Preliminary Report on Patentability," for PCT Application No. PCT/US2019/066358 mailed Jun. 24, 2021 (12 pages).

"International Preliminary Report on Patentability," for PCT Application No. PCT/US2019/068397 mailed Jul. 8, 2021 (9 pages).

"International Preliminary Report on Patentability," for PCT Application No. PCT/US2020/026435 mailed Oct. 14, 2021 (8 pages).

"International Search Report and Written Opinion," for PCT Application No. PCT/US2017/069026 mailed Apr. 3, 2018 (16 pages).

"International Search Report and Written Opinion," for PCT Application No. PCT/US2017/069035 mailed Apr. 3, 2018 (16 pages).

"International Search Report and Written Opinion," for PCT Application No. PCT/US2018/017944 mailed Apr. 26, 2018 (12 pages).

"International Search Report and Written Opinion," for PCT Application No. PCT/US2019/060296 mailed Apr. 14, 2020 (14 pages).

"International Search Report and Written Opinion," for PCT Application No. PCT/US2019/060298 mailed Apr. 28, 2020 (20 pages).

(56) References Cited

OTHER PUBLICATIONS

"International Search Report and Written Opinion," for PCT Application No. PCT/US2019/066358 mailed Jun. 23, 2020 (18 pages).
"International Search Report and Written Opinion," for PCT Application No. PCT/US2019/068397 mailed Apr. 14, 2020 (14 pages).
"International Search Report and Written Opinion," for PCT Application No. PCT/US2020/026435 mailed Jul. 9, 2020 (12 pages).
"Invitation to Pay Additional Fees and, Where Applicable, Protest Fee," for PCT Application No. PCT/US2019/066358 mailed Mar. 5, 2020 (12 pages).
EP Search Report dated Oct. 8, 2018 from EP App. No. 18171323.1, 10 pages.
PathVU Mobile App, Pathway Accessibility Solutions, Inc., Pittsburgh, Pennsylvania [retrieved on Jun. 19, 2018. Retrieved from the Internet:<URL: http://www.pathvu.com/>; 6 pgs.
Barber & Stockwell "Manual of Electronystagmography," 1980, C.V. Mosby Company, St. Louis, Missouri, Cover page, copyright page, and table of contents; total of 3 pages.
Buatois, et al."Posturography and Risk of Recurrent Falls in Healthy Non-Institutionalized Persons Aged Over 65," Gerontology, 2006;52(6):345-352 (8 pages).
Choi, W. J., et al. "Effect of Neck Flexor Muscle Activation on Impact Velocity of the Head During Backward Falls in Young Adults," Clinical Biomechanics 49 (2017), pp. 28-33.
Coburn, Courtney, et al. "The Comfort Bud: Designed with Patients in Mind," Starkey Hearing Technologies Product Sheet, 2017 (2 pages).
Da Costa, et al. "Can Falls Risk Prediction Tools Correctly Identify Fall-Prone Elderly Rehabilitation Inpatients? A Systematic Review and Meta-Analysis," PLoS ONE, 2012; 7(7):e41061 (8 pages).
El Miedany, et al. "Falls Risk Assessment Score (FRAS): Time to Rethink," Journal of Clinical Gerontology & Geriatrics, 2011: 2011; 2(1):21-26 (6 pages).
Farrell, Lisa, et al. "Vestibular Rehabilitation: An Effective, Evidence-Based Treatment," Vestibular Disorders Association 2015 (11 pages).
Hendrich, Ann L., et al ."Validation of the Hendrich II Fall Risk Model: A Large Concurrent Case/Control Study of Hospitalized Patients," Applied Nursing Research, vol. 16, No. 1 Feb. 2003: pp. 9-21 (13 pages).
Hendrich, Ann, et al. "Hospital Falls: Development of a Predictive Model for Clinical Practice," Applied Nursing Research, vol. 8, No. 3 Aug. 1995: pp. 129-139 (11 pages).
Horak "Postural Orientation and Equilibrium: What do we Need to Know About Neural Control of Balance to Prevent Falls?," Age and Ageing, 2006; 35-S2:ii7-ii11 (5 pages).
Howcroft, et al. "Review of Fall Risk Assessment in Geriatric Populations using Inertial Sensors," J Neuroeng Rehab, 2013; 10:91 (12 pages).
Howcroft, et al. "Understanding Dynamic Stability From Pelvis Accelerometer Data and the Relationship to Balance and Mobility in Transtibial Amputees," Gait Posture, 2015; 41(3): 808-812 (5 pages).
Klenk, et al. "Conceptualizing a Dynamic Fall Risk Model Including Intrinsic Risks and Exposures," JAMDA, 2017; 18:921-927 (7 pages).
Leake, Jason Llewellyn "Fall Detectors for People with Dementia," University of Bath Student Thesis, Jun. 2016 (364 pages).
Marschollek, et al. "Predicting In-Patient Falls in a Geriatric Clinic: a Clinical Study Combining Assessment Data and Simple Sensory Gait Measurements," Z Gerontol Geriatr, 2009; 42(4):317-321 (6 pages).
Oliver "Falls Risk-Prediction Tools for Hospital Inpatients. Time to Put Them to Bed?," Age and Ageing, 2008; 37:248-250 (3 pages).
Rumalla, et al. "The Effect of Hearing Aids on Postural Stability," Laryngoscope, 2015; 125(3):720-723 (4 pages).
Salisbury, Joseph P., et al. "Patient Engagement Platform for Remote Monitoring of Vestibular Rehabilitation with Applications in Concussion Management and Elderly Fall Prevention," 2018 IEEE International Conference on Healthcare Informatics, pp. 422-423.

Viikki "Machine Learning on Otoneurological Data: Decision Trees for Vertigo Diseases," Academic Dissertation, University of Tampere, Finland, 2002; 84 pages.
Yang, et al. "Fall Risk Assessment and Early-Warning for Toddler Behaviors at Home," Sensors, 2013; 13:16985-17005 (21 pages).
Zheng, et al. "Effect of postural changes on lower limb blood volume detected with non-invasive pholoplethysmography," Journal of Medical Engineering & Technology, vol. 32, No. 5, Sep./Oct. 2008, pp. 358-364 (7 pages).
"Final Office Action," mailed Jul. 22, 2024, for U.S. Appl. No. 18/139,671 21 pages.
"Notice of Allowance," for U.S. Appl. No. 17/673,461 mailed Jul. 12, 2024 (14 pages).
"Response to Non-Final Office Action," for U.S. Appl. No. 18/139,671 filed Jul. 3, 2024 (10 pages).
"Notice of Allowance," for U.S. Appl. No. 15/895,311 mailed Aug. 14, 2024 (17 pages).
"Response to Final Office Action," U.S. Appl. No. 15/858,680 filed Jul. 24, 2024 (12 pages).
"Non-Final Office Action," for U.S. Appl. No. 15/858,680 mailed Sep. 26, 2024 (16 pages).
"Non-Final Office Action," for U.S. Appl. No. 17/628,436 mailed Sep. 29, 2024 (56 pages).
"Final Office Action," for U.S. Appl. No. 15/858,680 mailed May 6, 2024 (25 pages).
"Final Office Action," for U.S. Appl. No. 15/895,311 mailed Mar. 12, 2024 (15 pages).
"Final Office Action," for U.S. Appl. No. 17/673,461 mailed Mar. 13, 2024 (22 pages).
"Non-Final Office Action," for U.S. Appl. No. 15/858,680 mailed Dec. 18, 2023 (32 pages).
"Non-Final Office Action," for U.S. Appl. No. 15/895,311 mailed Oct. 12, 2023 (13 pages).
"Non-Final Office Action," for U.S. Appl. No. 17/673,461 mailed Sep. 27, 2023 (43 pages).
"Non-Final Office Action," for U.S. Appl. No. 18/139,671 mailed Apr. 11, 2024 (42 pages).
"Response to Final Office Action," for U.S. Appl. No. 15/858,680 filed Sep. 21, 2023 (14 pages).
"Response to Final Office Action," for U.S. Appl. No. 15/895,311 filed Jun. 12, 2024 (8 pages).
"Response to Final Office Action," for U.S. Appl. No. 17/673,461 filed Jun. 13, 2024 (10 pages).
"Response to Non-Final Office Action," for U.S. Appl. No. 15/895,311 filed Jan. 12, 2024 (9 pages).
"Response to Non-Final Office Action," for U.S. Appl. No. 17/673,461 filed Dec. 27, 2023 (11 pages).
"Response to Non-Final Rejection," mailed on Dec. 18, 2023, for U.S. Appl. No. 15/858,680, submitted via EFS-Web on Mar. 18, 2024, (12 pages).
Corvera, Jorge, et al. "Evaluation of the Vestibular Autorotation Test (VAT) for Measuring Vestibular Oculomotor Reflex in Clinical Research," Archives of Medical Research 31 (2000), 384-387 (4 pages).
"Non-Final Office Action," for U.S. Appl. No. 18/139,671 mailed Nov. 18, 2024 (24 pages).
"Response to Final Office Action," for U.S. Appl. No. 18/139,671 filed Oct. 10, 2024 (11 pages).
"Response to Final Office Action," for U.S. Appl. No. 15/858,680 filed Dec. 20, 2024 (9 pages).
"Response to Final Office Action," for U.S. Appl. No. 17/628,436 filed Dec. 20, 2024 (12 pages).
"Final Office Action," for U.S. Appl. No. 18/139,671 mailed Mar. 18, 2025 (24 pages).
"Notice of Allowance," for U.S. Appl. No. 15/858,680 mailed Feb. 3, 2025 (18 pages).
"Response to Non-Final Office Action," for U.S. Appl. No. 18/139,671 filed Feb. 12, 2025 (11 pages).
"Communication pursuant to Article 94(3)," for European Patent Application No. 20754071.7 mailed May 12, 2025 (5 pages).
"Non-Final Office Action," for U.S. Appl. No. 17/628,436 mailed Jul. 22, 2025 (25 pages).

(56) References Cited

OTHER PUBLICATIONS

"Non-Final Office Action," for U.S. Appl. No. 18/037,248 mailed Jun. 12, 2025 (35 pages).

"Notice of Allowance," for U.S. Appl. No. 18/139,671 mailed Aug. 5, 2025 (15 pages).

"Response to Final Office Action," for U.S. Appl. No. 18/139,671, filed on Jun. 17, 2025 (10 pages).

"Response to Final Office Action," or U.S. Appl. No. 17/628,436, filed on Jun. 30, 2025 (12 pages).

"Response to Final Office Action," for U.S. Appl. No. 17/628,436, filed on Jul. 11, 2025 (13 pages).

"Response to Non-Final Office Action," for U.S. Appl. No. 18/037,248, filed on Aug. 29, 2025 (11 pages).

"Communication per Article 94(3) EPC," for European Application No. 20720723.4, mailed Oct. 21, 2025, (7 pages).

"Final Office Action," for U.S. Appl. No. 17/628,436 mailed Jan. 2, 2026 (27 pages).

"Final Office Action," for U.S. Appl. No. 18/037,248 mailed Nov. 28, 2025 (26 pages).

"Non-Final Office Action," for U.S. Appl. No. 18/033,937 mailed Nov. 28, 2025 (17 pages).

"Response to Non-Final Office Action," for U.S. Appl. No. 17/628,436, filed on Oct. 21, 2025 (13 pages).

"Response to Final Office Action," for U.S. Appl. No. 17/600,370, filed on Oct. 9, 2025 (15 pages).

"Communication per Article 94(3) EPC," Citation for European Application No. 20720723.4, mailed Feb. 23, 2026 (24 pages).

"Response to Final Office Action," for U.S. Appl. No. 17/628,436, filed on Apr. 2, 2026 (12 pages).

"Response to Final Office Action," for U.S. Appl. No. 18/037,248, filed on Mar. 2, 2026 (12 pages).

"Response to Non-Final Office Action," for U.S. Appl. No. 18/033,937, filed on Mar. 2, 2026 (10 pages).

"Non-Final Office Action," for U.S. Appl. No. 17/628,436 mailed May 27, 2026 (27 pages).

* cited by examiner

MONITORING SYSTEM AND METHOD OF USING SAME

This application is being filed as a PCT International Patent application on Apr. 2, 2020, in the name of Starkey Laboratories, Inc., a U.S. national corporation, applicant for the designation of all countries, and Justin R. Burwinkel, a U.S. Citizen, and Buye Xu, a Chinese Citizen, and Jason A. Galster, a U.S. Citizen, and Lauren Sculthorpe-Petley, a Canadian Citizen, and Peter J. Tetrick, a U.S. Citizen, and Sourav K. Bhunia, a U.S. Citizen, and Peggi S. Cross, a U.S. Citizen, and Martin F. McKinney, a U.S. Citizen, inventor(s) for the designation of all countries, and claims priority to U.S. Provisional Patent Application No. 62/828,766, filed Apr. 3, 2019, the contents of which are herein incorporated by reference in its entirety.

BACKGROUND

Activity monitoring and classification of patients and subjects can provide caregivers with real-time notice of medically-relevant events such as falls. For example, automated fall detection can detect whether a subject has fallen and send information regarding the fall to a caregiver or first responder. Maintaining postural control and preventing such falls are of importance for the elderly. Falls are the second leading cause of accidental or unintentional injury deaths worldwide and are especially prevalent in the elderly. Currently, individuals are often inadequately prepared to protect themselves from falls or other serious injuries as the onset of such events can come without perceptible warning. Further, maintaining postural equilibrium, i.e., prevention of a fall, involves stabilization of the body's center of mass during both self-initiated and externally triggered disturbances to postural stability during normal daily activities. Maintaining such equilibrium can be accomplished by limiting the motion of the center of mass within the base of support formed by and around the feet. Postural equilibrium is maintained through multisensory inputs. For example, loss of sensory input in the feet due to neuropathy can increase the risk of a fall, even though the necessary motor control for a corrective action of repositioning the feet can still be intact. Similarly, low vision or reduced ranges of hearing can prevent an individual from detecting hazards within their environment such that they can avoid them.

SUMMARY

In general, the present disclosure provides various embodiments of a monitoring system. The monitoring system can include two or more sensors that are adapted to detect a characteristic of a subject of the system and generate data representative of the characteristic. The system can further include a controller operatively connected to the first and second sensors and adapted to determine statistics of an overall condition state of the subject over a monitoring time period based upon confirmation of one or more condition substates.

In one aspect, the present disclosure provides a monitoring system that includes first and second sensors each adapted to detect a characteristic of a subject of the system and generate data representative of the characteristic of the subject, where the characteristic includes at least one of a physiological characteristic or contextual information of the subject; and a controller operatively connected to the first and second sensors. The controller is adapted to receive data representative of a first characteristic of the subject from the first sensor, determine statistics for a first condition substate of the subject over a monitoring time period based upon the data received from the first sensor, receive data representative of a second characteristic of the subject from the second sensor, and determine statistics for a second condition substate of the subject over the monitoring time period based upon the data received from the second sensor. The controller is further adapted to compare the statistics of the first condition substate to the statistics of the second condition substate, confirm the first condition substate of the subject if the first condition sub state is substantially similar to the second condition substate, and determine the statistics of an overall condition state of the subject over the monitoring time period based upon the confirmed first condition substate.

In another aspect, the present disclosure provides a method that includes receiving data representative of a first characteristic of a subject from a first sensor, determining statistics for a first condition substate of the subject over a monitoring time period based upon the data received from the first sensor, receiving data representative of a second characteristic of the subject from a second sensor, determining statistics for a second condition substate of the subject over the monitoring time period based upon the data received from the second sensor. The method further includes comparing the statistics of the first condition substate to the statistics of the second condition substate, confirming the first condition substate of the subject if the first condition substate is substantially similar to the second condition substate, and determining the statistics of an overall condition state of the subject over the monitoring time period based upon the confirmed first condition substate.

These and other aspects of the present disclosure will be apparent from the detailed description below. In no event, however, should the above summaries be construed as limitations on the claimed subject matter, which subject matter is defined solely by the attached claims, as may be amended during prosecution.

BRIEF DESCRIPTION OF THE DRAWINGS

Throughout the specification, reference is made to the appended drawings, where like reference numerals designate like elements, and wherein.

DETAILED DESCRIPTION

Figure 1:
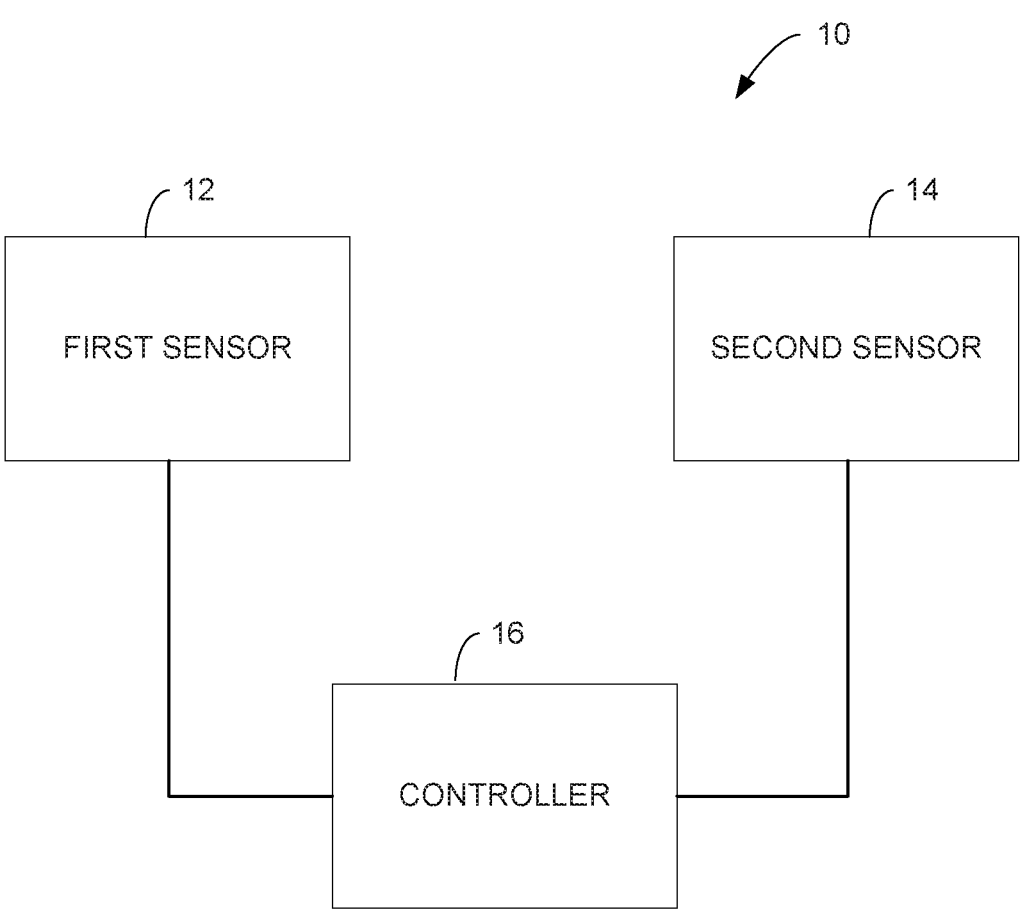
FIG. 1 is a schematic diagram of one embodiment of a monitoring system.

In general, the present disclosure provides various embodiments of a monitoring system. The monitoring system can include two or more sensors that are adapted to detect a characteristic of a subject of the system and generate data representative of the characteristic. The system can further include a controller operatively connected to the first and second sensors and adapted to determine statistics of an overall condition state of the subject over a monitoring time period based upon confirmation of one or more condition substates.

Activity monitoring systems can be inaccurate due to individual variability among subjects and poor fitting devices. Further, monitoring systems that detect falls can be prone to falsely identifying such falls because of non-fall events such as sitting down. Such false alarms can unnecessarily escalate alarm and emergency responses from caregivers and first responders. Further, a subject of an automated fall detection system may become more fearful of falling, less forthcoming about their falls risk, or avoid using the fall detection system altogether. Fall detection accuracy is also important for a falls risk estimation model that can account for previous fall events detected by the system.

One or more embodiments of monitoring systems described herein can utilize two or more operatively connected sensors and devices to provide redundancy that can improve the accuracy of automated activity decisions. This redundancy results from either (a) use of different types of sensors, leading to similar conclusions that can be drawn (e.g., an accelerometer and a barometer can each indicate a sudden downward change in elevation) or (b) from a duplicity of similar sensors (e.g., an accelerometer disposed on a right ear of a subject corroborates a conclusion based upon measurements from an accelerometer disposed on a left ear of the subject).

One or more embodiments of monitoring systems described herein can utilize unique combinations of sensors for activity monitoring and fall detection that can enhance the classification of measurable events. Various inputs related to activity monitoring and fall detection may be detected either (a) leading up to a fall, (b) during a fall event, or (c) following a fall event. For example, one or more embodiments of monitoring systems described herein can utilize one or more of the following techniques and devices for at least one of activity monitoring or fall detection:

electroencephalography (EEG) that can detect the onset of syncope (i.e., loss of consciousness), onset of a stroke or aneurysm, onset of a seizure, loss of alertness, onset of pain, etc.;

EEG that can detect body movements that are not correlated with the subject's cognitive intent or that require greater degrees of cognitive load to perform (e.g., navigating obstacles, Parkinson's Disease, etc.);

electrooculography (EOG) and videooculography (VOG) that can detect onset of nystagmus (i.e., indication of dizziness or intoxication);

electrocardiography (EKG or ECG) that can detect onset of cardiac infarcts (i.e., heart attacks), palpitations, pericarditis, angina, etc.;

blood pressure sensors that can detect the onset of orthostatic hypotension and orthostatic syncope;

blood sugar level sensors that can detect the onset of hypoglycemia;

blood oxygen level sensors that can detect the onset of hypoxia;

carbon monoxide sensors that can corroborate symptoms of dizziness or syncope due to environmental factors;

thermometers that can monitor changes in core body temperature or head temperature, or can detect an increased likelihood that a fall has occurred due to environmental factors;

microphones that can detect an impact caused by a fall, vocal utterances related to distress, or corroborate presentation of the Tullio phenomenon (i.e., dizziness caused by loud sounds);

ambient light sensors that can detect an increased likelihood that a fall has occurred due to various environmental factors;

proximity sensors that can detect the presence of tripping hazards; and radio signal sensors that can communicate with nearby hazard beacons (either virtual or physical) or act as proximity sensors within a mesh network of other devices.

Output from various sensors can be used as raw data or classifications can be made based upon the sensor data. Further, one or more state models can utilize various statistical methods to determine which of the available inputs typically occur together given particular outcomes. These techniques can be applied, e.g., to activity classification and analysis and fall detection. Further, data from two or more sensors can assist medical professionals with classifying a fall event to determine if a subject has lost consciousness and the likelihood that a traumatic brain injury has occurred.

In addition, crowd-sourced data can be stored and accessed from the cloud. This information can assist in identifying specific locations or types of locations, events, groups of people, etc., where falls or other physical activities are likely to occur. For example, outdoor areas may include uneven ground that may cause falls or near-falls to occur. Further, falls may also commonly occur within indoor areas as well. Data regarding these outdoor and indoor areas can be automatically populated or manually populated by subjects to provide a warning to others. This information in turn can be utilized to form virtual hazard beacons as is described, e.g., in U.S. Patent Publication No. 2018/0233018A1, entitled FALL PREDICTION SYSTEM INCLUDING A BEACON AND METHOD OF USING SAME, the contents of which are herein incorporated by reference in its entirety.

Any suitable system can be utilized for at least one of activity classification and fall detection. For example, FIG. 1 is a schematic diagram of one embodiment of a monitoring system 10. The system 10 includes a first sensor 12, a second sensor 14, and a controller 16 operatively connected to the first and second sensors. As used herein, the term "operatively connected" means that an element or component can be connected to another element or component using any suitable technique or techniques such that information can be shared between such components. In one or more embodiments, one or both of the first sensor 12 and second sensor 14 can be operatively connected to the controller 16 by a wire or cable, wirelessly using any suitable wireless protocol, optically, over the internet, a mesh network, etc.

The monitoring system 10 can be utilized with any suitable device or application. For example, in one or more embodiments, the system 10 can be associated with any suitable body-worn device, e.g., body-worn device 100 of FIG. 2. In one or more embodiments, the system 10 can be disposed in a room or building and be adapted to monitor one or more individuals proximate to the system using any suitable technique or techniques. In one or more embodiments, the system 10 can utilize at least one of lidar, facial recognition software, camera systems, hazard beacons, Bluetooth-based directional arrival software, geotagging, radio frequency identification (RFID), light sensors, and the like to identify and track an individual located in the room or building and provide at least one of physiological data or contextual information regarding the individual to the controller 16 for further processing as is described herein.

The sensors 12, 14 can be disposed in any suitable location. In one or more embodiments, the sensors 12, 14 can be a component of electronic components 120 of the body-worn device 100 of FIG. 2, e.g., sensors 134, 136. In one or more embodiments, the sensors 12, 14 can be disposed outside of the housing of a hearing device and operatively coupled to the device and the controller 16 using any suitable technique or techniques. In one or more embodiments, sensors 12, 14 can be disposed within one or both ears and outside the ear of the subject. In one or more embodiments, the sensors 12, 14 can be disposed within one or more devices worn by one or more individuals other than the subject of interest. In one or more embodiments, the sensors 12, 14 can be disposed within one or more physical hazard beacons, e.g., as described in U.S. Patent Publication No. 2018/0233018 A1.

Each of the first and second sensors 12, 14, is adapted to detect a characteristic of a subject of the system and generate data representative of the characteristic of the subject. Any suitable characteristic or characteristics of the subject can be detected by the sensors 12, 14. In one or more embodiments, the characteristic includes at least one of a physiological characteristic or contextual information of the subject. As used herein, the term "physiological characteristic" refers to information regarding the subject's physiological state, e.g., at least one of a determined fall risk, inertial sensor data, heart rate information, blood pressure information, drug concentration information, blood sugar level, body hydration information, neuropathy information, blood oximetry information, hematocrit information, cortisol level, body temperature, age, sex, gait or postural stability attribute, vision, hearing, eye movement, neurological activity, head movement, or the like. In one or more embodiments, a physiological characteristic can include psychological data representative of a psychological state such as a fear of falling. A psychological state can, in one or more embodiments, be detected from data representative of the physiological characteristic (i.e., physiological data) or combinations of physiological characteristics such as heart rate, core body temperature, or cortisol levels. Further, in one or more embodiments, the physiological data can include, in part or in combination, one or more inputs provided by the subject in response to one or more queries.

Further, as used herein, the term "contextual information" refers to data representative of a context within which the subject is disposed or will be disposed at a future time. In one or more embodiments, data representative of the contextual information (i.e., contextual data) can include at least one of weather condition, environmental condition, sensed condition, location, velocity, acceleration, direction, hazard beacon, type of establishment occupied by the subject, camera information, or presence of stairs, etc. One or more hazard beacons can provide contextual data to the system 10. Such hazard beacons can include physical or virtual beacons as described, e.g., in U.S. Patent Publication No. 2018/0233018 A1.

Although depicted as including two sensors 12, 14, the system 10 can include any suitable number of sensors, e.g., 1, 2, 3, 4, 5, or more sensors. Each of the first and second sensors 12, 14 can include any suitable sensor or sensors. For example, each of the sensors 12, 14 can include at least one of an accelerometer, barometer, gyroscope, heart rate sensor, blood pressure sensor, magnetometer, EOG sensor, EEG sensor, VOG sensor, EKG or ECG sensor, blood sugar sensor, blood oxygen sensor, light sensor, sweat sensor, pupillometry sensor, cerumen sensor, cortisol sensor, body temperature sensor, humidity sensor, air quality sensor, carbon monoxide sensor, microphone, proximity sensor, GPS, telecoil, magnetic sensor, or radio signal sensor, or combinations thereof. The sensors 12, 14 can be adapted to detect any suitable characteristic of the subject, e.g., at least one of a physiological characteristic and contextual information of the subject. For example, the physiological characteristic can include at least one of body position, the position of specific body parts, eye movement, body temperature, heart rate, EEG, or skin impedance, or combinations thereof. Further, for example, the contextual information can include at least one of ambient temperature, moisture/humidity, sound, light intensity, terrain, elevation, ambient oxygen levels, pollutants, toxins, or carbon monoxide levels, or combinations thereof.

The first sensor 12 is adapted to detect a first characteristic of the subject and generate data (e.g., physiological data or contextual data) representative of the first characteristic. Further, the second sensor 14 is adapted to detect a second characteristic of the subject and generate data (e.g., physiological data or contextual data) representative of the second characteristic. The first and second characteristics of the subject can be any suitable characteristic, e.g., at least one of a physiological characteristic or contextual information of the subject. The first and second characteristics can include any suitable characteristic. The first characteristic detected by the first sensor 12 can be the same as or different from the second characteristic detected by the second sensor 14. For example, in one or more embodiments, the first characteristic detected by the first sensor 12 can be eye movement of the subject and the second characteristic detected by the second sensor 14 can be head movement of the subject.

Operatively connected to the first and second sensors 12, 14 is the controller 16. The controller 16 can include any suitable controller. Further, the controller 16 can include any suitable electronic components or elements. The controller 16 is adapted to receive data representative of a first characteristic of the subject from the first sensor 12; determine statistics for a first condition substate of the subject over a monitoring time period based upon the data received from the first sensor; receive data representative of a second characteristic of the subject from the second sensor 14; determine statistics for a second condition substate of the subject over the monitoring time period based upon the data received from the second sensor; compare the statistics of the first condition substate to the statistics of the second condition substate; confirm the first condition substate of the subject if the first condition sub state is substantially similar to the second condition substate; and determine the statistics of an overall condition state of the subject over the monitoring time period based upon the confirmed first condition substate.

As used herein, the term "data" can include a single datum or a plurality of data values or statistics. The term "statistics" can include any appropriate mathematical calculation or metric relative to data interpretation, e.g., probability, confidence interval, distribution, range, or the like. Further, as used herein, the term "monitoring time period" means a period of time over which the first and second characteristics of the subject are measured and statistics for the first and second condition substates are determined. The monitoring time period can be any suitable length of time, e.g., 1 millisecond, 1 second, 10 seconds, 30 seconds, 1 minute, 10 minutes, 30 minutes, 1 hour, etc.

The first and second substates can each include any suitable substates that can be utilized to determine the overall condition state. In one or more embodiments, each of the first and second substates can include at least one of body posture, body motion, location, direction, subject's activity, or mental substate. The first condition substate can be the same as or different from the second condition substate.

Although described as including first and second substates, the controller 16 is operable to determine statistics for any suitable number of substates. For example, in one or more embodiments, the controller 16 is further adapted to determine statistics for a third condition substate of the subject over a second monitoring time period based upon the data received from the first sensor, and determine statistics for a fourth condition substate of the subject over the second monitoring time period based upon the data received from the second sensor. The third and fourth condition substates can be the same as or different from one or more of the first and second condition substates.

Any suitable technique or techniques can be utilized to determine statistics for the various substates, e.g., direct statistical analyses of time series data from the sensors, differential statistics, comparisons to baseline or statistical models of similar data and substates, etc. Such techniques can be general or individual-specific and represent long-term or short-term behavior. These techniques could include standard pattern classification methods such as Gaussian mixture models, clustering as well as Bayesian approaches, neural network models and deep learning.

Further, the controller 16 is adapted to compare statistics of a condition substate (e.g., the first condition substate) and the statistics of another condition substate (e.g., the second condition substate) using any suitable technique or techniques. For example, substate similarity and dissimilarity can be measured directly via standard statistical metrics such normalized Z-score, or similar multidimensional distance measures (e.g. Mahalanobis or Bhattacharyya distance metrics), or through similarities of modeled data and machine learning. These techniques can include standard pattern classification methods such as Gaussian mixture models, clustering as well as Bayesian approaches, neural network models, and deep learning.

Any suitable technique or techniques can be utilized by controller 16 to confirm a condition substate (e.g., the first condition substate) of the subject if the first condition sub state is substantially similar to the second condition substate. As used herein the term "substantially similar" means that, upon comparison, the sensor data are congruent or have statistics fitting the same statistical model, each with an acceptable degree of confidence. The threshold for the acceptability of a confidence statistic may vary depending upon the subject, sensor, sensor arrangement, substate, combination of substates, context, condition, etc. In one or more embodiments, the first condition substate can be confirmed by comparing sensor data or applying the sensor data to a statistical model for one or more substates. In one or more embodiments, the second condition substate can be confirmed if the second condition substate is substantially similar to the first condition substate. Any suitable technique or techniques can be utilized to confirm the second condition substate, e.g., the same techniques described herein regarding confirmation of the first condition substate.

The statistics of an overall condition state of the subject, over the monitoring time period, can be based upon the confirmed condition substate (e.g., first condition substate) by utilizing any suitable technique or techniques, e.g., standard pattern classification methods such as Gaussian mixture models, clustering, hidden Markov models, as well as Bayesian approaches, neural network models, and deep learning. As used herein, the term "overall condition state" refers to the predicted or realized status of the subject. Examples of an overall condition state may include an activity classification such as sitting, walking, running, jumping, falling intentionally, falling unintentionally, and the like.

The controller 16 can be adapted to determine the statistics of any suitable number of overall condition states of the subject over the monitoring time period. For example, in one or more embodiments, the controller 16 can further be adapted to compare the statistics of the third condition substate to the statistics of the fourth condition substate; confirm the third condition substate of the subject if the third condition substate is substantially similar to the fourth condition substate; and determine the statistics of a second overall condition state of the subject over the second monitoring time period based upon the confirmed third condition substate. Any suitable technique or techniques can be utilized to determine the statistics of the second overall condition state, e.g., the same techniques utilized to determine the statistics of the overall condition state.

The controller 16 can also be adapted to compare the statistics of the first overall condition state to the statistics of the second overall condition state. Any suitable technique or techniques can be utilized to compare the statistics of two or more overall condition states. e.g., Gaussian mixture models or Hidden Markov Models to learn and classify multiple sets of activities and/or stages of walking stability or falling. In one or more embodiments, ongoing activity can be continuously classified or monitored, and a fall prevention output can be generated based upon this classified activity.

In one or embodiments, the controller 16 is further adapted to determine one or more of a fall risk value and fall risk statistic based upon the determined overall condition state of the subject. Any suitable technique or techniques can be utilized to determine one or more of a fall risk value and fall risk statistic, e.g., the techniques described in U.S. Patent Publication No. 2018/0228404 A1, entitled FALL PREDICTION SYSTEM AND METHOD OF USING SAME; and U.S. Patent Application Ser. No. 62/785,295, entitled PREDICTIVE FALL EVENT MANAGEMENT SYSTEM AND METHOD OF USING SAME, the contents of which are herein incorporated by reference in their entirety.

In one or more embodiments, the controller 16 can be adapted generate a fall prevention output responsive to satisfaction of the fall condition. Any suitable fall prevention output can be provided that can assist in mitigating the risk of the subject falling, e.g., one or more of an audible alert, visual alert, or tactile alert provided to the subject. For example, the subject can be warned of the subject acting on a predicted behavior when the predicted risk associated with the predicted behavior crosses a threshold for alerting the subject. In one or more embodiments, the subject can be advised of suitable options or alternatives to acting on a particular predicted behavior to protect the subject from engaging in unnecessary risky behaviors. In one or more embodiments, the subject can be given directions or advice to mitigate their risks. In one or more embodiments, the use of virtual reality or augmented reality such as those described, e.g., in U.S. Patent Publication No. 2018/0233018A1 can be used to assist the subject in avoiding potential risks.

In one or more embodiments, the fall prevention output can include initiating a mitigation therapy or corrective measures e.g., a balance training regimen. The fall prevention output can further include controlling or modifying one or more features and actions of a mobility device, an assistive device, or an exoskeleton.

In one or more embodiments, the fall prevention output can include one or more modifications of an environmental context of the subject. Any suitable environmental contexts can be modified to satisfaction of a predicted fall condition. For example, the fall prevention output can include modifying, via mesh networks or the internet of things (IoT), e.g., the lighting within an area proximate to the subject or within an area where the subject is predicted to be. Similarly, the fall prevention output can include modifying the temperature, oxygen mix, humidity, or air quality of an area proximate to the subject or within an area where the subject is predicted to be. Further, in one or more embodiments, the fall prevention output can include transmission of one or more of the physiological data and the contextual data to one or more of a caregiver, a medical professional, a database, or the subject.

In one or more embodiments, the fall prevention output can also include adapting one or more of a monitoring system setting such that the system is more likely to indicate that a fall has occurred if the predicted fall risk statistics crossed a certain threshold leading up to the occurrence in question as described, e.g., as described in U.S. Patent Application Ser. No. 62/780,223, entitled HEARING ASSISTANCE SYSTEM WITH ENHANCED FALL DETECTION, the contents of which are herein incorporated by reference in its entirety. In one or more embodiments, the adaptation of system settings can be applied transitorily such that the system is only more likely to indicate that a fall has occurred for a period of seconds or minutes. In one or more embodiments, the adaptation of system settings can be applied over a longer period of time.

The controller 16 can further be adapted to determine a balance event of the subject if the statistics of an overall condition state indicates one or more of an unintentional loss of balance or postural stability and vestibular disturbance. Any suitable technique or techniques can be utilized to determine a balance event, e.g., the techniques described in U.S. Patent Application Ser. No. 62/785,295.

The system 10 can be utilized with any suitable body-worn device for the subject that can be worn in any suitable location on the body of the subject, including but not limited to, a wearable hearing device such as headphones, a wrist-worn device such as a smartwatch, a patch disposed on any portion of a body of the subject, glasses, etc. The body-worn device can be implanted. Further, the body-worn device can, in one or more embodiments, be integrated into or otherwise disposed in a body part prothesis, mobility assistance device, or exoskeleton.

In one or more embodiments, the body-worn device can include a hearing assistance device such as behind-the-ear (BTE), in-the-ear (ITE), in-the-canal (ITC), or completely-in-the-canal (CIC) type hearing instrument. It is understood that behind-the-ear type hearing instruments can include devices that reside substantially behind the ear or over the ear. Such devices can include hearing instruments with receivers associated with the electronics portion of the behind-the-ear device or hearing instruments of the type having receivers in the ear canal of the subject. Such devices are also known as receiver-in-the-canal (RIC) or receiver-in-the-ear (RITE) hearing devices. In one or more embodiments, the body-worn device can include a cochlear implant (including its processor) or a bone-conduction or otherwise osseointegrated hearing device. It is understood that other body-worn devices not expressly stated herein can fall within the scope of the present subject matter. the system 10 can be utilized with any suitable number of body-worn devices, e.g., two or more body-worn devices. For example, in one or more embodiments, the system 10 can be utilized with a left hearing device that is adapted to be acoustically connected to the subject's left ear and a right hearing device that is adapted to be acoustically connected to the subject's right ear. In one or more embodiments, the left hearing device can electrically communicate with the right hearing device using any suitable technique or techniques.

Figure 2:
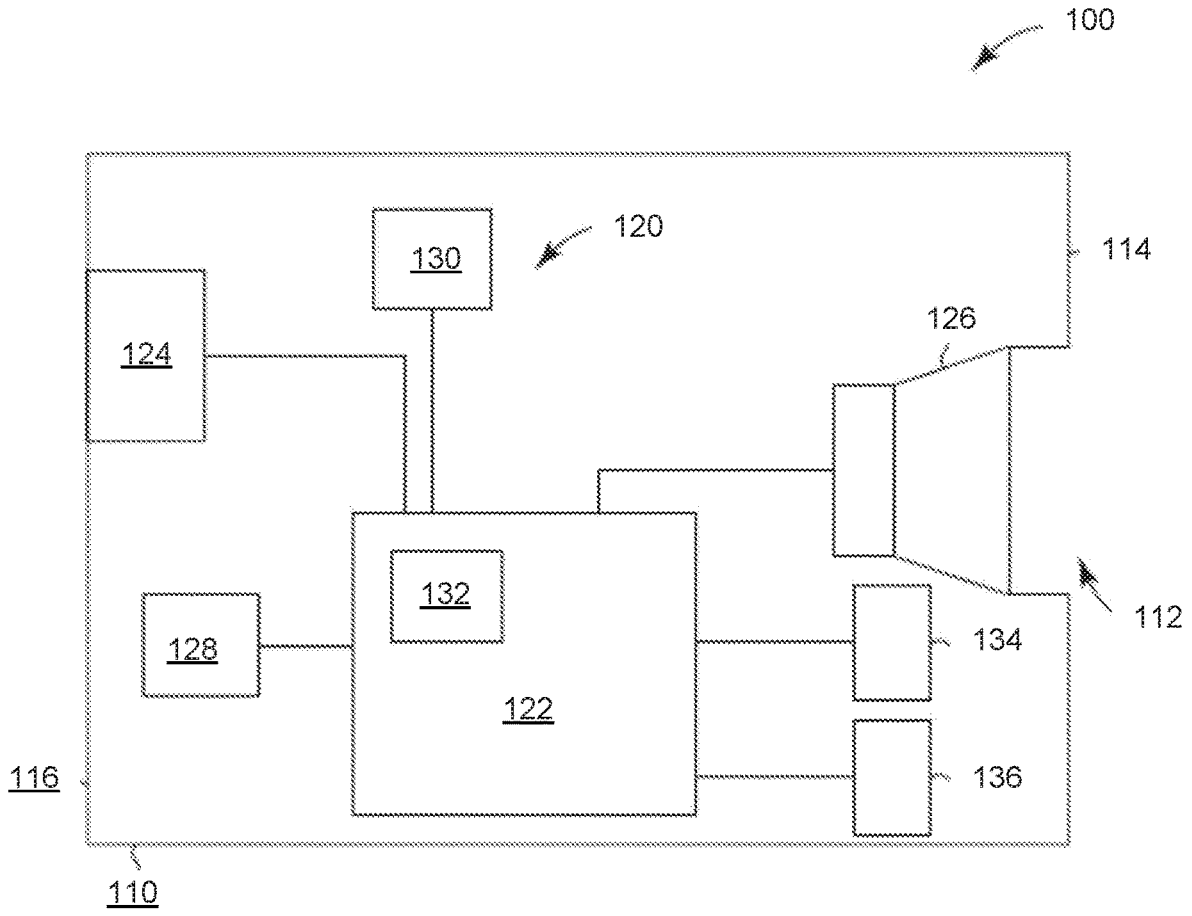
FIG. 2 is a schematic diagram of a body-worn device that utilizes the system of FIG. 1.

The body-worn device can include any suitable electronic components or circuitry. In one or more embodiments, the body-worn device can include hearing assistance components. For example, FIG. 2 is a schematic diagram of one embodiment of a body-worn device 100. The device 100 includes a housing 110 and hearing assistance components 120 disposed within the housing. Hearing assistance components 120 can include any suitable device or devices, e.g., integrated circuits, power sources, microphones, receivers, etc. For example, in one or more embodiments, the components 120 can include a controller 122 (e.g., controller 16 of FIG. 1), a microphone 124, a receiver 126 (e.g., speaker), a power source 128, an antenna 130, and one or more sensors 134, 136 (e.g., first and second sensor 12, 14 of FIG. 1). The microphone 124, receiver 126, power source 128, antenna 130, and sensors 134, 136 can be electrically connected to the controller 122 using any suitable technique or techniques. In one or more embodiments, the body-worn device can be adapted to provide the subject with auditory information, feedback, or guidance. In one or more embodiments, the device 100 can be adapted to accept verbal or gestural input from the subject. In one or more embodiments, encephalography (EEG) sensor data can be utilized to infer e.g., the subject's intentions.

Any suitable controller 122 can be utilized with the body-worn device 100, e.g., the same controller or controllers described herein regarding controller 16 of system 10 of FIG. 1. For example, the controller 122 can be adapted to employ programmable gains to adjust the output of the device 100 to a patient's particular hearing impairment. The controller 122 can be a digital signal processor (DSP), microprocessor, microcontroller, other digital logic, or combinations thereof. The processing can be done by a single processor or can be distributed over different devices. The processing of signals described herein can be performed using the controller 122 or over different devices.

In one or more embodiments, the controller 122 is adapted to perform instructions stored in one or more memories 132. Various types of memory can be used, including volatile and nonvolatile forms of memory. In one or more embodiments, the controller 122 or other processing devices execute instructions to perform a number of signal processing tasks. Such embodiments can include analog components in communication with the controller 122 to perform signal processing tasks, such as sound reception by the microphone 124, or playing of sound using the receiver 126.

In general, digital hearing devices include a controller or processor. In such devices, programmable gains our audiometric filters can be employed to adjust the hearing device output to a subject's particular hearing impairment or preferences. The controller 122 (and controller 16 of FIG. 1) can be a digital signal processor (DSP), microprocessor, microcontroller, other digital logic, or combinations thereof. The processing can be performed by a single processor or can be distributed over different devices. The processing of signals referenced in this application can be performed using the processor or other different devices. Processing can be done in the digital domain, the analog domain, or combinations thereof. Processing can be done using subband processing techniques. Processing can be done using frequency domain or time domain approaches. Some processing can involve both frequency and time domain aspects. For brevity, in some examples drawings can omit certain blocks that perform frequency synthesis, frequency analysis, analog-to-digital conversion, digital-to-analog conversion, amplification, buffering, and certain types of filtering and processing. In various embodiments, the processor is adapted to perform instructions stored in one or more memories, which can or cannot be explicitly shown. Various types of memory can be used, including volatile and nonvolatile forms of memory. In various embodiments, the processor or other processing devices execute instructions to perform a number of signal processing tasks. Such embodiments can include analog components in communication with the processor to perform signal processing tasks, such as sound reception by a microphone, or playing of sound using a receiver (i.e., in applications where such transducers are used). In various embodiments, different realizations of the block diagrams, circuits, and processes set forth herein can be created by one of skill in the art without departing from the scope of the present subject matter.

The hearing assistance components 120 can also include the microphone 124 that is electrically connected to the controller 122. Although one microphone 124 is depicted, the components 120 can include any suitable number of microphones. Further, the microphone 124 can be disposed in any suitable location within the housing 110. For example, in one or more embodiments, a port or opening can be formed in the housing 110, and the microphone 124 can be disposed adjacent the port to receive audio information from the subject's environment.

Any suitable microphone 124 can be utilized. In one or more embodiments, the microphone 124 can be selected to detect one or more audio signals and convert such signals to an electrical signal that is provided to the controller 122. Although not shown, the controller 122 can include an analog-to-digital convertor that converts the electrical signal from the microphone 124 to a digital signal.

Electrically connected to the controller 122 is the receiver 126. Any suitable receiver can be utilized. In one or more embodiments, the receiver 126 can be adapted to convert an electrical signal from the controller 122 to an acoustic output or sound that can be transmitted from the housing 110 to the subject. In one or more embodiments, the receiver 126 can be disposed adjacent an opening 112 disposed in a first end 114 of the housing 110. As used herein, the term "adjacent the opening" means that the receiver 126 is disposed closer to the opening 112 in the first end 114 than to a second end 216 of the housing 110.

The power source 128 is electrically connected to the controller 122 and is adapted to provide electrical energy to the controller and one or more of the other hearing assistance components 120. The power source 128 can include any suitable power source or power sources, e.g., a battery. In one or more embodiments, the power source 128 can include a rechargeable battery. In one or more embodiments, the components 120 can include two or more power sources 128.

The components 120 can also include the optional antenna 130. Any suitable antenna or combination of antennas can be utilized. In one or more embodiments, the antenna 130 can include one or more antennas having any suitable configuration. For example, antenna configurations can vary and can be included within the housing 110 or be external to the housing. Further, the antenna 130 can be compatible with any suitable protocol or combination of protocols. In one or more embodiments, the components 120 can also include a transmitter that transmits electromagnetic signals and a radio-frequency receiver that receives electromagnetic signals using any suitable protocol or combination of protocols.

For example, in one or more embodiments, the body-worn device 100 (or any other body-worn device described herein) can be connected to one or more external devices using, e.g., Bluetooth, Wi-Fi, magnetic induction, mesh networks, etc. For example, in one or more embodiments, the body-worn device 100 can be wirelessly connected to the Internet using any suitable technique or techniques. Such connection can enable the body-worn device 100 to access any suitable databases, including medical records databases, cloud computing databases, location services, etc. In one or more embodiments, the body-worn device 100 can be wirelessly connected utilizing the Internet of Things (IoT) such that the hearing device can communicate and share data with, e.g., one or more hazard beacons, one or more cameras disposed in proximity to the subject, motion sensors, room lights, air conditioning and heating controllers, etc. Further, in one or more embodiments, the body-worn device 100 can access weather information via the Internet or a mesh network using any suitable technique or techniques such that the subject can be informed of potentially hazardous weather conditions.

In one or more embodiments, the body-worn device 100 can include the first sensor 134 and the second sensor 136. Although depicted as including two sensors 134, 136, the body-worn device 100 can include any suitable number of sensors, e.g., 1, 2, 3, 4, 5, or more sensors. The sensors 134, 136 can include any suitable sensor or sensors, e.g., the same sensors described herein regarding sensors 12, 14 of system 10 of FIG. 1. The first sensor 134 can include the same sensor as the second sensor 136. In one or more embodiments, the first sensor 134 includes a sensor that is different from that of the second sensor 136. The sensors 134, 136 can be operatively connected to the controller 122 using any suitable technique or techniques.

In one or more embodiments, the first sensor 134 is operatively connected to the body-worn device 100 and adapted to detect a first characteristic of the subject and generate data (e.g., physiological data or contextual information) representative of the first characteristic. In one or more embodiments, the second sensor 136 is operatively connected to the body-worn device 100 and adapted to detect a second characteristic of the subject and generate data (e.g., physiological data or contextual information) representative of the second characteristic. The first and second characteristics can include any suitable characteristic, e.g., the same characteristic or characteristics described herein regarding sensors 12, 14 of system 10 of FIG. 1. The first characteristic detected by the first sensor 134 can be the same as or different from the second characteristic detected by the second sensor 136. For example, in one or more embodiments, the first characteristic detected by the first sensor 134 can be eye movement of the subject and the second characteristic detected by the second sensor 136 can be head movement of the subject.

Returning to FIG. 1, the monitoring system 10 can be utilized to receive input information and determine the statistics of one or more overall condition states of the subject or the monitoring time period. In one or more embodiments, the system 10 can be utilized to receive input information from any suitable source to determine the statistics of the overall condition state. The input information can be provided using any suitable sensor, device, or database. For example, the input information can be provided to the controller 16 by the sensors 12, 14, the system 10, manually by one or more of the subject, a caregiver, and a medical professional, or obtained from other systems via wired or wireless connections to system 10.

Further, the monitoring system 10 can provide any suitable outputs that can be based on the overall condition state or states. Any suitable output or outputs can be provided by the system 10, e.g., notifications, reports, IoT triggers (e.g., activating room lighting), treatments to the subject of the system 10, etc. In one or more embodiments, the system 10 can be utilized to detect head impact, check with the subject for consciousness, and inform one or more of the subject, caregiver, and medical professional of the detection of a head impact and level of consciousness of the subject.

As mentioned herein, the system 10 can utilize any suitable sensor configuration. For example, the system 10 can be utilized to detect and confirm Tullio's Phenomenon in a subject. Tullio's Phenomenon is characterized by loud external sounds or the subject's own voice causing dizziness that is evidenced with nystagmus eye movement. To detect and confirm this Phenomenon, the sensors 12, 14 of the system can include one or more of a microphone, eye movement sensor (e.g., electronystagmography (ENG), or videonystagmography (VNG) using a camera in smartglasses or on smartphone, etc.), own-voice sensor (e.g., accelerometer in the ear, microphone array, etc.), and an IMU sensor adapted to detect postural adjustments in response to the sound detected at the microphone.

Further, in one or more embodiments, the system 10 can be utilized to detect and confirm a loss of balance of the subject. The sensors 12, 14 can include one or more of an IMU sensor adapted to detect rapid stepping, sway, short-term change in walking stride/pattern, etc. (preceding a fall or near fall event), an EEG sensor (EEG can suggest that the brain is attempting to make the reflexive movements (e.g., rapid stepping) needed to recover from lost balance (preceding a fall or near fall event)), an eye movement sensor adapted to detect sway or abnormal stepping when there is an indication of nystagmus/loss of balance (preceding a fall or near fall event), and a microphone adapted to detect (acoustically) the presence of rapid stepping and when there is an indication of nystagmus/loss of balance (preceding a fall or near fall event).

Further, differentiation between reflexive and voluntary control of posture and movement can be detected and confirmed by the system 10 utilizing an IMU sensor combined with an EEG sensor. In such an embodiment, EEG data from the EEG sensor can suggest that the brain is attempting to make certain muscle movement. The system can determine if such EEG data corresponds with subject activity that's being measured by the IMU sensor. A mismatch between EEG data and IMU data can suggest a neurological problem.

The system 10 can also be utilized to detect and confirm a hypotensive event. For example, heart rate sensors can be used to detect heart rate variability to predict an orthostatic hypotensive event. Such hypotensive event can be confirmed by data from a skin temperature sensor to detect vasoconstrictor failure due to inadequate release of norepinephrine in neurogenic orthostatic hypotension.

Figure 3:
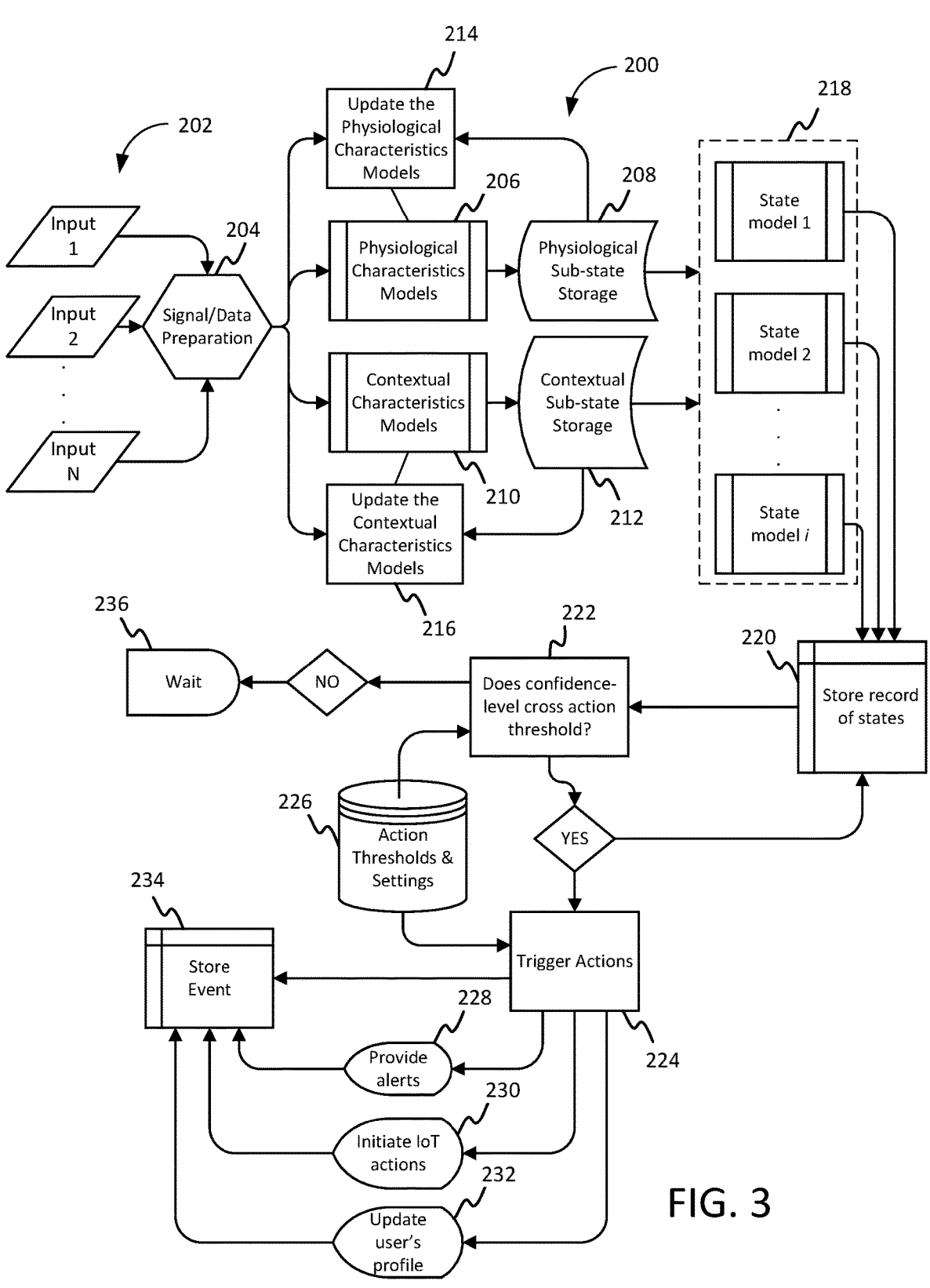
FIG. 3 is a flowchart of one embodiment of a method that can be utilized with the monitoring system of FIG. 1.

As described herein, the monitoring system 10 can utilize any suitable technique or techniques to determine statistics of one or more overall condition states of a subject of the system. For example, FIG. 3 is a flowchart of one embodiment of a method 200 for determining statistics of an overall condition state of a subject. The method 200 can be implemented using any suitable device or system, e.g., the monitoring system 10 of FIG. 1. Although described in reference to system 10 of FIG. 1, the method 200 can be utilized with any suitable device or system. In one or more embodiments, controller 16 of system 10 of FIG. 1 can be adapted to perform method 200. Further, the controller 16 can be adapted to perform the method 200 through firmware, software, etc. In one or more embodiments, the controller 16 can be or include an application-specific integrated circuit (ASIC) that includes the method 200.

Method 200 includes receiving inputs 202 at 204 for signal/data preparation. Any suitable inputs 202 can be received. In one or more embodiments, the inputs can be data representative of a first characteristic of a subject from the first sensor 12. Further, in one or more embodiments, data representative of a second characteristic of the subject can be received from the second sensor 14 as one or more inputs. In one or more embodiments, one or both of the first characteristic data and second characteristic data can include physiological data representative of a physiological characteristic of the subject of the system 10 over a monitoring time period. Further, one or both of the first characteristic data and second characteristic data can include contextual information representative of contextual information of the subject over the monitoring time period. Medical/health reports regarding the subject can also be provided as inputs 202. Any suitable databases containing, e.g., calendar data, reminder data, and data relative to actions of an artificial intelligence can also be provided as inputs 202. Further, group data from the cloud can also be provided as inputs at 202.

Such data can be prepared at 204 utilizing any suitable technique or techniques. In one or more embodiments, data from inputs 202 can be, e.g., filtered, time stamped, assigned metadata memory locations, and combinations thereof, at 204.

At 206, statistics for a first condition substate of the subject can be determined over a monitoring time period based upon the data received from the first sensor 12 and stored at 208. Any suitable technique or techniques can be utilized to determine the statistics for the first condition substate. For example, one or more pattern recognition machine learning techniques such as Hidden Markov Models (HMMs), Bayesian models, non-linear regressions, decision trees, support vector machines, neural networks, etc. can be applied to input data 202 to predict future physiological and contextual states based upon, at least in part, one or more of present and historical data. During a learning stage, prepopulated group data or laboratory data can be utilized to form the basis of training one or more pre-trained models. As the system collects data about the subject over time, one or more of these models can be updated using any suitable training techniques.

For example, a particular model at 206 can be trained or continuously adapted at 214 to learn the effects that a specific medication has on an individual, over time, based on data from a group of individuals. The model can be further updated, for a specific subject, as specific data relative to the severity and timing of any observable changes to the subject that is collected. In this example, an observable change can relate to one or more characteristics of the subject's gait and postural stability that can be observed or monitored using any suitable sensor arrangement. In one or more embodiments, the time at which the subject will ingest a particular medication can be predicted based upon any suitable contextual data e.g., historical, physiological, or historical contextual data, scheduled reminders, push notifications, location information, etc. Further, a particular model at 210 can be trained or continuously adapted at 216 based on the subject's contextual information such as historical environment and location data, over time, to recognize patterns such that a prediction of the subject's future location can be made at 210. For example, historical fall event and balance event data from one or more of the individual or a group of individuals, at a given location, can further inform the risk factor associated with the location the individual is predicted to be at in a future time.

Statistics for a second condition substate of the subject can be determined at 210 over a monitoring time period based upon the data received from the second sensor 14 and stored at 212. Any suitable technique or techniques can be utilized to determine the statistics for the second condition substate, e.g., the same techniques utilized to determine statistics for the first condition substate. Although not shown, additional substates can be determined based upon additional data from the first and second sensors 12, 14 or one or more additional sensors.

The first condition substate 206 can be updated at 214 based upon one or more of the inputs 202. For example, changes in gait such as increased postural sway, irregular stride, lower foot clearance, and decreased walking speed can be detected, using any suitable means, and can indicate that a new lower limb limitation can increase the individual's risk for stumbling over uneven walking paths.

The second substate model 210 can also be updated at 216 based upon one or more of the inputs 202 and the contextual risk factor values or statistics. For example, changes in weather conditions or geographical locations of the subject can be factored into the contextual factor models 210 using any suitable technique or techniques.

At 218, statistics of the first condition substate can be compared to the statistics of the second condition substate using any suitable technique or techniques. In one or more embodiments, statistics of the third condition substate can be compare to the statistics of the fourth condition substate at 218 using any suitable technique or techniques.

Also at 218, the first condition substate of the subject can be confirmed using any suitable technique or techniques. For example, the first condition substate can be confirmed if the first condition substate is substantially similar to the second condition substate. Further the third condition substate of the subject can be confirmed at 218 using any suitable technique or techniques. For example, the third condition substate can be confirmed if the first condition substate is substantially similar to the forth condition substate.

The statistics of one or more overall condition states of the subject over the monitoring time period based upon the confirmed one or more condition substates can be determined at 218. For example, the statistics of an overall condition state of the subject over the monitoring time period based upon the confirmed first condition substate can be determined at 218. Any suitable technique or techniques can be utilized to determine the statistics of the overall condition state. Further, the statistics of the second overall condition state of the subject over the second monitoring time period based upon the confirmed third condition substate can also be determined at 218 using any suitable technique or techniques.

In one or more embodiments, one or more of a fall risk value and fall risk statistic based upon the determined overall condition state of the subject can be determined at 218 using any suitable technique or techniques. For example, in one or more embodiments, a risk or probability value of a fall can be determined that can be based on a predetermined formula or formulas that can be derived from experimental data. The formula can also be entirely learned or modified through various machine learning approaches. For example, when a fall event is detected, the method 200 can send postural data collected before the event by one or more sensors 12, 14, e.g., to a cloud server. In one or more embodiments, data from the subject and other subjects can be used to train a regression model or deep neural network to estimate the risk of a fall for an individual subject. One or more of the sub-models can be generated from analytics or machine learning of larger group data using any suitable technique or techniques, e.g., regression, steady-state, Bayesian, classification trees, Volterra, support vector machine, Gaussian mixture, neural network techniques, and combinations thereof.

The sub-models can provide an estimate or probability of the a given substate being an accurate reflection of the user of the subject and learn the subject's norms regarding motion patterns and health/physiological information. Inputs for generating the sub-models can either be obtained based on clinical evaluations and medical history or be learned by the monitoring system 10 from one or more inputs provided by various types of sensors, e.g., sensor 12, 14, and responses to queries.

For example, motion patterns of the subject and changes to such patterns can be estimated and monitored based on the outputs from one or more of an inertial measurement unit (IMU) sensor, GPS sensor barometer, magnetometer, EEG sensor, camera, etc. The motion of the subject can include sway amplitude and speed while walking, speed and trajectory when sitting down or standing up, speed and radius when turning, stride length, symmetry and variance, frequency of walks, length or distance of walks, reaction speed, etc.

In one or more embodiments, one or more of periodic assessments of functional balance ability, muscle strength, perceived balance efficacy, fear of falling, or functional reaction speed of the subject can be performed by the method 200 and queried to the subject or a third party. In one or more embodiments, one or more of results of periodic functional balance ability, muscle strength, perceived balance efficacy, fear of falling, or functional reaction speed of the subject can be entered into the manually by either the subject or a third party. As an illustrative example, the results of e.g., the Timed Up and Go (TUG) test can be calculated either by the instrumented body-worn device or entered by the individual or a third-party observer.

In one or more embodiments, physiological data that can be provided as inputs to the sub-models at 218 include heart rate, blood pressure, blood sugar, blood oxygen, core body temperature, etc., and can be monitored utilizing any suitable sensor or sensors 12, 14. All such inputs and how they change over time can be monitored and used to estimate whether a fall condition is satisfied (i.e., how prone the subject is to a fall).

For example, one of the sub-models at 218 can evaluate postural stability (i.e., displacement of the head of the subject in three dimensions) of the subject to determine a fall risk value based on monitoring of the subject at 206. Any suitable sensor or sensors 12, 14 can be utilized to determine postural stability, e.g., one or more of an accelerometer, gyroscope, microphone, barometer, optical sensor, and bioelectrical sensor. In one or more embodiments, the sensors 12, 14 can include an accelerometer and a gyroscope as the primary sensors for postural balance and fall-risk monitoring and the other sensors can be secondary sensors. For example, a secondary sensor can include a microphone that can be used for detecting foot-falls or a fall event. Further, a barometer can be used to detect stair climbing. In addition, an optical sensor can be used for measuring heart rate and other biosignals. A bioelectric sensor can be used for monitoring electro-, cardio-, encephalo-, occulo-, and myo-graph signals from any location on the head and body of the subject.

In general, there can be multiple activities and postures during which one may fall down, most commonly walking and standing, transitions between postures such as movement between standing and sitting, etc. Further, there can be identifiable physiological events that precede the fall, such as postural hypotension.

One or more physiological sensors 12, 14 can be employed to identify a "prodrome" of a postural instability. Some possible techniques of using this sensor information for this purpose can be used individually or in combination.

For example, in one or more embodiments, the sensors 12, 14 can include one or more of an accelerometer and a gyroscope. Signals form the sensors, 12, 14 can be used to compute and monitor a deviation from a stable position and a velocity with which such deviation takes place. In one or more embodiments, the controller 16 can utilize the signal inputs from the sensors 12, 14 to generate a measure of postural stability. Such postural stability can be included in one or more physiological data inputs at 202. Postural stability can be recorded during normal daily activities, including standing, walking, and climbing stairs. Postural stability can also be recorded during structed activities and functional tests, e.g., during performance of a TUG test or the like. A threshold of normal stability can be established based on clinical postural stability testing or during a subject-initiated initialization involving one or more of these activities. Measurements in case of a recorded fall can be used to adjust the threshold, if appropriate.

Acceleration of the head of the subject while walking is complex, with the most prominent feature in the unprocessed accelerometer signal being that of the footfall. Adding to this complexity can be stabilization of the head by the neck. Footfall signals can be diminished by neck stabilization but still can be detectable. Vestibular-ocular reflexes can also be measured as the eye will attempt to stabilize the individual's visual field with each step. In one or more embodiments, head oscillation in three dimensions (anteroposterior (AP), lateral, and vertical) can be measured. Components of the displacement and the velocity in each dimension can be computed as measures of the postural stability. Although generally correlated and constrained by the body, the head can move relatively independently, which introduces artifacts. To mitigate these artifacts, in one or more embodiments, the velocity and displacement of the head oscillation are computed only when the pitch, yaw and/or roll motions of the head a slower than some predefined thresholds. Artifacts related to head movements can also be mitigated, by the controller, through the integration of sensor inputs of body-worn sensors placed on the chest, trunk, waist, etc. The values or statistics can depend upon the speed and type of body movement.

In one or more embodiments, the controller 16 can be adapted to determine a fall condition by measuring a maximum displacement between a longitudinal axis of the subject and a normal to the earth's surface as a function of time. Further, in one or more embodiments, the controller 16 can be adapted to determine the fall condition by measuring a maximum velocity of displacement between a longitudinal axis of the subject and a normal to the earth's surface.

Fall risk thresholds related to safe postural stability or limits of stability can be established by balance testing in a clinical setting or by subject-conducted self-directed tests. A fall risk signal or other fall risk output can be generated based on single or multiple threshold crossings.

Parameters of postural stability, i.e., balance metrics, and fall risk values or statistics can be of interest to one or more of the subject, caregivers such as the family members, and medical professionals. Balance metrics and fall risk values or statistics can be monitored e.g., daily or hourly and transmitted to various parties. The system can continuously monitor the subject, and once a fall risk threshold is exceeded, a fall risk output such as a discrete audio alert can be provided to the subject.

In laboratory conditions, head worn IMU sensors can be utilized to characterize small motions (e.g., sway) that can be important for balance evaluation. The orientation of the IMU sensors, however, is highly controlled and well calibrated in the laboratory. In practice, when subjects are wearing two hearing devices, proper alignment of the IMU sensors at each side of the head is desired. Any suitable technique or techniques can be utilized to align the sensors 12, 14 in both left and right hearing devices of the system 10, e.g., the techniques described in U.S. patent application Ser. No. 15/331,130, filed Oct. 21, 2016, and entitled HEAD RELATED TRANSFER FUNCTION INDIVIDUALIZATION FOR HEARING DEVICE, the contents of which are herein incorporated by reference in its entirety. In one or more embodiments, a technique can be utilized to compensate for the orientation mismatch between two hearing devices so that the IMU sensors on both sides of the head can be collaboratively aligned with the head orientation and used to derive postural stability information.

In one or more embodiments, the fall risk value based upon postural stability can be determined by first detecting that the subject is walking. One or more artifacts from the sensors 12, 14 caused by foot impact can be filtered out using any suitable technique or techniques. Postural stability can be determined using any suitable technique or techniques. Velocity components of such postural stability can also be determined using any suitable technique or techniques. In one or more embodiments, the fall risk value can be based upon walking speed, distance walked, frequency of walks, duration of walks, frequency of successful postural transitions, speed of postural transitions, or the like and other activity classifications, and combinations thereof.

A composite sensitivity parameter of the contribution of the sensors 12, 14 (e.g., one or more accelerometers) to the overall fall risk value or statistic can be determined using any suitable technique or techniques. In one or more embodiments, the sensitivity of the fall risk value or statistics to an amplitude of the postural stability can be determined using, e.g., one or more of a subject input after a near-fall event, a balance study, and fall detection. The sensitivity of the fall risk value or statistics to the stability velocity at a pre-determined postural stability can be determined using, e.g., one or more subject inputs after a near-fall event, a balance test, fall detection or the like. Further, the sensitivity of the fall risk value to a statistically determined combination of the postural stability and the stability velocity can also be determined.

In one or more embodiments, postural stability, sway velocity and other posture, walking and fall-related information can be routinely transmitted to healthcare professionals. The subject's posture while standing and walking, actual fall events, and subject-indicated near-fall events can also be transmitted to healthcare professionals.

If the fall risk value or statistics crosses a fall risk threshold, then an alert can be sent to one or more of the subject, caregiver, and medical professional. Such alerts can include instructions for how to prevent a fall from occurring.

In one or more embodiments, sensors 12, 14 having one or more accelerometers can be placed in both ears of the subject. Acceleration of the mid-point between the two ears, as opposed to that of one ear, can be calculated to determine postural stability. Further, false positives of fall detection can be reduced by ensuring both sensors 12, 14 follow the same nominal motion pattern. In addition, head rotation around the vertical axis i.e., the yaw, can also be determined and utilized to calculate the fall risk value.

In one or more embodiments, a fall condition can be determined by measuring eye movement of the subject. For example, the monitoring system 10 can detect eye movements and compare such eye movements to a baseline to determine whether a vestibular event is occurring that can increase the risk of fall. The sensors 12, 14 of the monitoring system 10 can include one or more eye movement sensors. In one or more embodiments, the system 10 can also include one or more sensors 12, 14 that can measure head movement of the subject. Data from such head movement sensors 12, 14 can be utilized to correlate with eye movement sensor data to determine the risk of a fall. Any suitable fall prediction system or device can be utilized to measure eye movement of a subject, e.g., the devices described in U.S. Pat. No. 9,167,356, issued Oct. 20, 2015, and entitled ELECTROOCULOGRAM AS A CONTROL IN A HEARING ASSISTANCE DEVICE, the contents of which are herein incorporated by reference in its entirety.

For example, in one or more embodiments, one or more inputs can be provided by one or more of the subject, the caregiver, and the physician. For example, one or more inputs can be provided by the subject in response to one or more queries provided, e.g., by the system 10, the caregiver, or the physician.

Outputs from the state models 218 can be stored at 220. Such outputs can include data that includes risk-level scaling and trends. At 222 a determination, for a future time, of whether an overall condition state satisfies one or more criteria can be made using any suitable technique or techniques. For example, each overall condition state can be assigned a confidence level using any suitable technique or techniques. The confidence level of each overall condition state can be compared to one or more thresholds to determine whether one or more outputs or actions are triggered at 224.

For example, reinforcement learning techniques can be applied at 224 to select the best possible output behavior strategy in a given situation. Reinforcement learning models can consider one or more of a predicted physiological risk factor, predicted contextual risk factor, historical physiological risk factor, historical contextual factor, predicted fall event, historical fall event, predicted balance event, historical balance events, and the like. In one or more embodiments, the reinforcement learning model can further consider the statistics of an overall condition state associated with historical data to optimize one or more outputs at 224. In one or more embodiments, determining whether the overall condition state threshold is satisfied at 222 includes applying a future fall risk value to a fall risk model. Such fall risk model can be developed from outputs from the fall risk prediction state models 218. In one or more embodiments, the system 10 can include several models: a physiological model, a contextual model, and a fall risk model. The fall risk model can use the output (e.g., state) of the physical model and contextual model as inputs to the fall risk model. The future fall risk value can be based upon the one or more future physiological states or contextual states. In one or more embodiments, the controller 16 can be adapted to determine at 222, for each of a plurality of future times, whether an anticipated fall condition is satisfied based upon one or more of the physiological data and contextual data. Further, in one or more embodiments, the controller 16 can be adapted to determine at 222, for a plurality of future times, whether an anticipated fall condition is satisfied based upon a combination of the physiological data and the contextual information. In one or more embodiments, the controller 16 can be adapted to determine at 222, for a plurality of future times, whether the fall condition is satisfied by determining a future fall risk value based upon the one or more future physiological states or contextual states.

Data related to thresholds can be stored at 226 and utilized at 222 to determine whether the overall condition state threshold has been satisfied at 222 and also utilized to generate outputs at 224.

If the overall condition state threshold has been met at 222, then the method 200 proceeds to 224, where one or more outputs responsive to satisfaction of one or more overall condition state thresholds can be provided to the subject. The output can include one or more outputs described herein. For example, a fall prevention output can be provided to the subject at 228 that includes one or more alerts that are provided to one or more of the subject, caregiver, and medical professional for proper diagnosis and treatment. Further, for example, an output can include initiating mitigation therapy at 230. Such mitigation therapy can include initiating a balance training regimen or corrective measure as described, e.g., in U.S. Patent Publication No. 2018/0317837A1, entitled HEARING ASSISTANCE DEVICE INCORPORATING VIRTUAL AUDIO INTERFACE FOR THERAPY GUIDANCE, the contents of which are herein incorporated by reference in its entirety. In one or more embodiments, the fall prevention output can include delivery or modification of a therapy or initiation of an intervention, e.g., activation of an exoskeleton worn by the subject. Further, the fall prevention output can include generating an IoT action at 232 such as sending one or more signals to one or more IoT devices proximate to the subject to help prevent the fall or otherwise protect the subject from injury, increasing an intensity of the ambient light for the subject's environment, etc. In one or more embodiments, an output can include a fall prevention output if the fall risk value or fall risk statistic crosses a fall risk threshold.

A particular instance of when the overall condition state threshold is satisfied at 222 and which outputs are generated at 224 can be stored at 234. Such data that is stored at 234 can be utilized to updated one or both of the physiological factor models at 214 or the contextual factor models at 216. Further, such data of a fall condition being met can be utilized to modify one or more of the fall risk prediction sub-models at 218.

If the overall condition state threshold has not been satisfied at 222, then the method 200 proceeds to a wait condition at 236.

All headings provided herein are for the convenience of the reader and should not be used to limit the meaning of any text that follows the heading, unless so specified.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements.

The words "preferred" and "preferably" refer to embodiments of the disclosure that may afford certain benefits, under certain circumstances; however, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a," "an," and "the" are not intended to refer to only a singular entity but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

As used in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

All references and publications cited herein are expressly incorporated herein by reference in their entirety into this disclosure, except to the extent they may directly contradict this disclosure. Illustrative embodiments of this disclosure are discussed and reference has been made to possible variations within the scope of this disclosure. These and other variations and modifications in the disclosure will be apparent to those skilled in the art without departing from the scope of the disclosure, and it should be understood that this disclosure is not limited to the illustrative embodiments set forth herein. Accordingly, the disclosure is to be limited only by the claims provided below.

What is claimed is:

1. A monitoring system comprising:
a first sensor adapted to detect a first characteristic of a subject and generate data representative of the first characteristic of the subject, wherein the first characteristic comprises a first physiological characteristic of the subject
a second sensor adapted to detect a second characteristic of the subject and generate data representative of the second characteristic of the subject;
a controller operatively connected to the first and second sensors, wherein the controller is adapted to:
receive data representative of the first characteristic of the subject from the first sensor;
determine statistics for a first condition substate of the subject over a monitoring time period based upon the data received from the first sensor;
receive data representative of the second characteristic of the subject from the second sensor;
determine statistics for a second condition substate of the subject over the monitoring time period based upon the data received from the second sensor;
compare the statistics of the first condition substate to the statistics of the second condition substate;

confirm the first condition substate of the subject when the first condition substate is substantially similar to the second condition substate; and
determine the statistics of an overall condition state of the subject over the monitoring time period based upon the confirmed first condition substate; and
utilize a machine learning model to determine a fall risk value based upon the determined overall condition state of the subject;
generate a fall prevention output when the fall risk value crosses a fall risk threshold, the fall prevention output comprising modifying, via mesh networks or the internet of things, the lighting within an area proximate to the subject;
wherein the machine learning model is further configured to predict a time at which the subject will ingest a particular medication based on location information, and to learn the effects that the particular medication has on the subject based on changes in the data representative of the first characteristic or data representative of the second characteristic in a time period after the time at which the subject is predicted to ingest the particular medication.

2. The system of claim 1, wherein each of the first and second condition substates comprises at least one of a body posture, mental, body motion, or sensory substate.

3. The system of claim 1, wherein the physiological characteristic comprises at least one of a determined fall risk statistic, inertial sensor data, heart rate information, blood pressure information, drug concentration information, blood sugar level, body hydration information, neuropathy information, blood oximetry information, hematocrit information, body temperature, age, sex, gait or postural stability attribute, vision, eye movement, geographic location, or head movement.

4. The system of claim 1, wherein the first sensor is operatively connected to the subject.

5. The system of claim 1, wherein the fall prevention output comprises a modification of an environmental context of the subject.

6. The system of claim 1, wherein the fall prevention output comprises transmission of the physiological data to one or more of a caregiver, a medical professional, a database, or the subject.

7. The system of claim 1, wherein the controller is further adapted to:
determine statistics for a third condition substate of the subject over a second monitoring time period based upon the data received from the first sensor;
determine statistics for a fourth condition substate of the subject over the second monitoring time period based upon the data received from the second sensor;
compare the statistics of the third condition substate to the statistics of the fourth condition substate;
confirm the third condition substate of the subject if the third condition substate is substantially similar to the fourth condition substate; and
determine the statistics of a second overall condition state of the subject over the second monitoring time period based upon the confirmed third condition substate.

8. The system of claim 1, wherein the controller is further adapted to determine a balance event of the subject when the statistics of the overall condition state indicates one or more of an unintentional loss of balance or postural stability and vestibular disturbance.

9. The system of claim 1, wherein the system is configured to update the machine learning model to include the effects that a specific medication has on an individual.

10. The system of claim 1, wherein the system is configured to update the machine learning model using specific data regarding the severity and timing of any observable changes to the subject that is collected, wherein the observable change can relate to one or more characteristics of the subject's gait and postural stability.

11. The system of claim 1, wherein the machine learning model is further configured to predict the time at which the subject will ingest the particular medication based on any of historical contextual data, scheduled reminders, and location information.

12. The system of claim 1, wherein the fall prevention output further comprises a modification of a temperature, oxygen mix, humidity, or air quality of the area proximate to the subject.

13. The system of claim 1, wherein the fall prevention output further comprises a modification of one or more features and actions of a mobility device, an assistive device, or an exoskeleton.

14. A method comprising:

receiving data representative of a first characteristic of a subject from a first sensor, wherein the first sensor comprises an inertial measurement unit (IMU);

determining statistics for a first condition substate of the subject over a monitoring time period based upon the data received from the first sensor;

receiving data representative of a second characteristic of the subject from a second sensor, wherein the second sensor comprises an electroencephalography (EEG) sensor;

determining statistics for a second condition substate of the subject over the monitoring time period based upon the data received from the second sensor;

comparing the statistics of the first condition substate to the statistics of the second condition substate;

confirming the first condition substate of the subject when the first condition substate is substantially similar to the second condition substate;

differentiating between reflexive and voluntary control of the subject's posture and/or movement using the IMU and the EEG sensor;

suggesting a neurological problem of the subject when the first condition substate of the subject contradicts the second condition substate of the subject;

determining the statistics of an overall condition state of the subject over the monitoring time period based upon the confirmed first condition substate, wherein the controller is further adapted to utilize a machine learning model to determine a fall risk value based upon the determined overall condition state of the subject; and generating a fall prevention output when the fall risk value crosses a fall risk threshold, the fall prevention output comprising modifying, via mesh networks or the internet of things, the lighting within an area proximate to the subject.

15. The method of claim 14, wherein each of the first and second condition substates comprises at least one of a body posture, mental substate, body motion, or sensory substate.

16. The method of claim 14, wherein the data representative of the first characteristic and the data representative of the second characteristic comprises at least one of physiological data and contextual information, wherein the fall prevention output comprises transmission of one or more of the physiological data and the contextual information to one or more of a caregiver, a medical professional, a database, or the subject.

17. The method of claim 14, further comprising:

determining statistics for a third condition substate of the subject over a second monitoring time period based upon the data received from the first sensor;

determining statistics for a fourth condition substate of the subject over the second monitoring time period based upon the data received from the second sensor;

comparing the statistics of a third condition substate to the statistics of a fourth condition substate;

confirming the third condition substate of the subject if the third condition substate is substantially similar to the fourth condition substate; and determining the statistics of a second overall condition state of the subject over the second monitoring time period based upon the confirmed third condition substate.

18. The method of claim 14, further comprising determining a balance event of the subject when the statistics of the overall condition state indicates one or more of an unintentional loss of balance or postural stability and vestibular disturbance.

19. The method of claim 14, wherein the first sensor comprises a microphone and the second sensor comprises an eye movement sensor, the method further comprising suggesting Tullio's Phenomenon in the subject when postural adjustments are detected by the second sensor in response to a sound detected by the first sensor.

* * * * *